(12) United States Patent
Qi

(10) Patent No.: US 10,143,719 B2
(45) Date of Patent: Dec. 4, 2018

(54) INHIBITORS OF VALOSIN-CONTAINING PROTEIN AND METHODS OF USE

(71) Applicant: CASE WESTERN RESERVE UNIVERSITY, Cleveland, OH (US)

(72) Inventor: Xin Qi, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 15/018,502

(22) Filed: Feb. 8, 2016

(65) Prior Publication Data

US 2016/0228492 A1    Aug. 11, 2016

Related U.S. Application Data

(60) Provisional application No. 62/113,063, filed on Feb. 6, 2015.

(51) Int. Cl.
*A61K 38/08* (2006.01)
*A61K 38/17* (2006.01)

(52) U.S. Cl.
CPC .......... *A61K 38/08* (2013.01); *A61K 38/1709* (2013.01)

(58) Field of Classification Search
CPC combination set(s) only.
See application file for complete search history.

(56) References Cited

PUBLICATIONS

Yang et al., PLoS ONE, 5(1):e8905, Jan. 2010.*

* cited by examiner

*Primary Examiner* — Kimberly Ballard
*Assistant Examiner* — Stacey N Macfarlane
(74) *Attorney, Agent, or Firm* — Tarolli, Sundheim, Covell & Tummino, LLP

(57) ABSTRACT

A method of inhibiting aberrant valosin-containing protein (VCP) accumulation in the mitochondria of a nerve cell includes administering to the nerve cell a therapeutic agent that inhibits the binding or complexing of VCP with a polyglutamine protein.

9 Claims, 9 Drawing Sheets

Specification includes a Sequence Listing.

INHIBITORS OF VALOSIN-CONTAINING PROTEIN AND METHODS OF USE

RELATED APPLICATION

This application claims priority from U.S. Provisional Application No. 62/113,063, filed Feb. 6, 2015, the subject matter of which is incorporated herein by reference in its entirety.

TECHNICAL FIELD

This application relates to compositions and methods for inhibiting aberrant Valosin-Containing Protein (VCP) accumulation in the mitochondria of nerve cells, and particularly relates to compositions and methods for treating diseases or disorders associated with aberrant VCP accumulation in the mitochondria of nerve cells.

BACKGROUND

There are a number of neurodegenerative polyglutamine diseases, for example Huntington's disease, spinocerebellar ataxia, and spinobulbar muscular atrophy (Kennedy's Disease), which are characterized by expanded genomic CAG sequences resulting in the synthesis and accumulation of polyglutamine tracts in brain proteins of unknown function (e.g., Huntingtin in Huntington's disease and ataxin in spinocerebellar ataxias) that are responsible for the neurologic problem. The CAG codon is translated into glutamine (Q). Proteins with expanded polyglutamine domains aggregate and aggregation is a pathologic hallmark of the polyglutamine repeat diseases (Hackam, A. S. et al. J Cell Biol 141, 1097-1105 (1998); Perez, M. K. et al. J Cell Biol 143, 1457-1470 (1998)). These polyglutamine length-dependent properties may arise from the ability of long polyglutamine domains to adopt unique three-dimensional conformations and serve to confer the disease proteins with a pathologic gain-of-function (Perutz, M. F. Trends Biochem Sci 24, 58-63 (1999); Lansbury, P. T. J. Proc Natl Acad Sci USA 96, 3342-3344 (1999)).

All diseases in the CAG repeat family show genetic anticipation, meaning the disease usually appears at an earlier age and increases in severity with each generation. Genetic anticipation is linked to increasing numbers of CAG repeats, which result from expansion of the unstable CAG sequence when reproductive cells divide to form eggs and sperm. In general, neurodegenerative disorders are progressive (i.e., their symptoms are not apparent until months or more commonly years after the disease has begun), and caused by an initial reduction of neuronal function, followed by a complete loss of function upon neuronal death.

Huntington's Disease (HD) is a devastating, degenerative brain disorder for which there is, at present, no effective treatment or cure. HD slowly diminishes the affected individual's ability to walk, think, talk and reason. Eventually, the person with HD becomes totally dependent upon others for his or her care. Huntington's Disease profoundly affects the lives of entire families: emotionally, socially and economically. Early symptoms of Huntington's Disease may affect cognitive ability or mobility and include depression, mood swings, forgetfulness, clumsiness, involuntary twitching and lack of coordination. As the disease progresses, concentration and short-term memory diminish and involuntary movements of the head, trunk and limbs increase. Walking, speaking and swallowing abilities deteriorate. Eventually the person is unable to care for him or herself. Death follows from complications, such as choking, infection or heart failure. HD typically begins in mid-life, between the ages of 30 and 45, though onset may occur as early as the age of 2. Children who develop the juvenile form of the disease rarely live to adulthood. HD affects males and females equally and crosses all ethnic and racial boundaries. Each child of a person with HD has a 50/50 chance of inheriting the fatal gene. HD is an autosomal dominant condition and thus everyone who carries the gene will develop the disease.

The Huntington's Disease (HD) gene was mapped to chromosome 4p16.3 in 1983 but eluded identification until 1993. When finally identified, the gene (IT15) was found to contain a CAG repeat within its 5'-end coding sequence (Cell 72:971-983). This CAG repeat is expanded in individuals with HD who may or may not be symptomatic. However, the presence of a CAG repeat expansion is found in virtually all symptomatic HD individuals (N. Engl. J. Med. 330:1401-1406).

Normal HD gene CAG repeats range from 10-29 repeats. Some normal individuals (<1%) have been found with intermediate HD gene CAG repeats of 30-35 repeats. Individuals affected with HD typically have at least one HD gene CAG repeat of 36 repeats or greater. It was also found that in a few rare instances (10 cases) individuals having repeats of 36-39 repeats had remained asymptomatic by standard clinical criteria at advanced age. In one exceptional case, a 95 year old patient had 39 repeats (Rubinsztein et. al., 1996; Am. J. Hum. Genet. 59:16-22). There is a tendency to an earlier age-of-onset of HD symptoms with increasing CAG repeat number. A review of 1,049 people (the majority of whom were symptomatic) has provided a determination of the likelihood of an age-of-onset for a given CAG repeat size for repeats between 39-50 repeats (Brinkman et al., 1997; Am. J. Hum. Genet. 60:1202-1210). The polyglutamine expansion results in the formation of insoluble, high molecular weight protein aggregates similar to those seen in Alzheimer's disease (Scherzinger et al., Cell 90:549-558 [1997]). Postmortem examination of the brains of patients suffering from Huntington's disease revealed that CAG repeat length positively correlates with the degree of DNA fragmentation within the afflicted striatum (Butterworth et al., Neurosci., 87:49-53 [1998]), indicating that neuronal degeneration observed in Huntington's disease may also occur through an apoptotic process.

Currently, physicians may prescribe a number of medications to help control emotional and movement problems associated with polyglutamine disorders caused by expanded genomic CAG nucleotides. Such medications include antipsychotic drugs, such as haloperidol, or other drugs, such as clonazepam, to alleviate choreic movements and also to help control hallucinations, delusions, and violent outbursts; fluoxetine, sertraline, nortriptyline, or other compounds may be prescribed for depression. Tranquilizers can help control anxiety and lithium may be prescribed to combat pathological excitement and severe mood swings. It is important to remember however, that while medicines may help keep these clinical symptoms under control, there is currently no treatment to stop or reverse the course of the disease.

Remacemide and Coenzyme Q10 have been tested for the treatment of HD but a large-scale clinical trial that tested the ability of these investigational drugs to slow the progression of Huntington's disease showed that neither drug resulted in any significant improvement for the patients. Remacemide blocks a neurotransmitter in the brain (the NMDA glutamate receptor) which has long been suspected of contributing to the death of brain cells in Huntington's disease. Coenzyme Q10 is a substance that occurs naturally in the body and plays a role in the function of mitochondria, the energy factories of human cells. It is also an anti-oxidant, meaning that it can neutralize potentially injurious oxygen-containing chemicals called free radicals, which may play a role in the nerve cell death that occurs in Huntington's disease. After one year of treatment, the disease seemed to progress more slowly in patients treated with Coenzyme Q10, however, the investigators concluded that overall the results were inconclusive as to whether there is real benefit from this drug (Neurology, Aug. 14, 2001; 57: 397).

SUMMARY

Embodiments described herein relate to methods of inhibiting valosin-containing protein (VCP) accumulation in mitochondria of a nerve cell and particularly relates to methods of treating a disorder associated with aberrant VCP accumulation by polyglutamine proteins in mitochondria of nerves cells in a subject in need thereof.

The methods can include administering to nerve cells of the subject a therapeutic agent that inhibits the binding or complexing of VCP with polyglutamine proteins. In some embodiments, the disorder can include a neurodegenerative disorder, such as a polyglutamine neurodegenerative disease. In other embodiments, the polyglutamine protein is mutant huntingtin protein (mtHtt) and the disorder is Huntington's disease.

In other embodiments, the therapeutic agent can include a therapeutic peptide. The therapeutic peptide can have at least about 75% sequence identity to about 8 to about 10 consecutive amino acids of an interaction site of VCP with the polyglutamine protein. In some embodiments, the therapeutic peptide can have an amino acid sequence that is at least about 75% identical to SEQ ID NO: 4. For example, the therapeutic peptide can have an amino acid sequence of SEQ ID NO: 3.

In other embodiments, the therapeutic agent can include a transport moiety that is linked to the therapeutic peptide and facilitates uptake of the therapeutic peptide by the nerve cell. The transport moiety can be, for example, an HIV Tat transport moiety.

In other embodiments, the therapeutic agent can be administered systemically to the subject being treated. For example, a therapeutic agent that includes a therapeutic peptide having an amino acid sequence of SEQ ID NO: 3, which is linked to a HIV Tat transport moiety, can be administered intravenously to a subject with Huntington's disease.

The amount of the therapeutic agent that is administered to the subject can be an amount effective to increase plasma levels of NAD+, FAD, and/or citrate in the subject.

(B) Mitochondrial and ER fractions were isolated from mouse HdhQ7 and HdhQ111 striatal cells. Protein levels of VCP were analyzed by Western blotting. VDAC and WFS1 were used as loading controls of mitochondria and ER. Data are mean±SE of three independent experiments. (C) Control siRNA (Con) and Htt siRNA (siHTT) were transfected in HdhQ7 and HdhQ111 cells, respectively. VCP levels were determined in mitochondrial fractions by Western blot analysis. VDAC was a loading control. Data are mean±SE of three independent experiments. (D) HdhQ7 and HdhQ111 mouse striatal cells were stained with anti-Tom20 (green, a mitochondrial marker) and anti-VCP (red) antibodies. Scale bars: 10 μm. VCP/Tom20 co-localization was examined using confocal microscopy. Pearson's co-efficiency was calculated. At least 100 cells per group were counted by an observer blind to experimental conditions. Data are mean±SE of three independent experiments.

(E) Mitochondria were isolated from the striatum of either HD transgenic mice R6/2 at the age of 9 weeks or YAC128 at the age of 6 months. n=6 mice/group. VCP levels were determined by Western blot (loading control: VDAC). Data are mean±SE. (F) Paraffin-embedded sections (5 μm thick) of caudate nucleus from three HD patients (ID: 2982, 2983 and 5413) and three normal subjects (ID: 623, 624 and 1533) were immune-stained with anti-VCP (red) and anti-Tom20 (green) antibodies. Localization of VCP on mitochondria was examined using confocal microscopy. Pearson's co-efficiency was calculated. Patient 2982 (56 years old, female), 2983 (30 years old, male), 5413 (43 years old, male) exhibited moderate neuronal loss in caudate nucleus and died of HD. The three normal subjects had no history of HD and other neurological diseases. Subject 623 (85 years old, male) and 624 (62 years old, female) were died of otosclerosis and subject 1533 (79 years old, female) died of spasmodic torticollis. The central nervous system of the three normal subjects showed no pathognomonic changes. Normal caudate nucleus and basal ganglia of these three subjects were observed. (G) Mitochondria, ER and cytosolic fractions (Ct) of HdhQ7 and HdhQ111 mouse striatal cells were subjected to immunoprecipitation (IP) with anti-VCP antibody, and immunoprecipitates were analyzed by immunoblotting (IB) with anti-VCP and anti-MAB2166 antibody (recognizes both wt and mtHtt, left panel) or anti-1C2 antibody (recognizes mtHtt, right panel). Note that polyQ protein above 250 kDa was shown in the right panel. Shown are representative blots from three independent experiments.

(H) Mitochondria, ER, and cytosolic fractions were isolated from striata of YAC128 and wildtype mice at the age of 6 months. IP with anti-VCP antibody followed by anti-1C2 antibody or anti-EM48 antibody was performed. The right panel indicates the purity of ER and mitochondrial fractions isolated from YAC128 mouse striatum. WFS1 and VDAC were used to label ER and mitochondria, respectively. n=4 mice/group.

Figure 2:
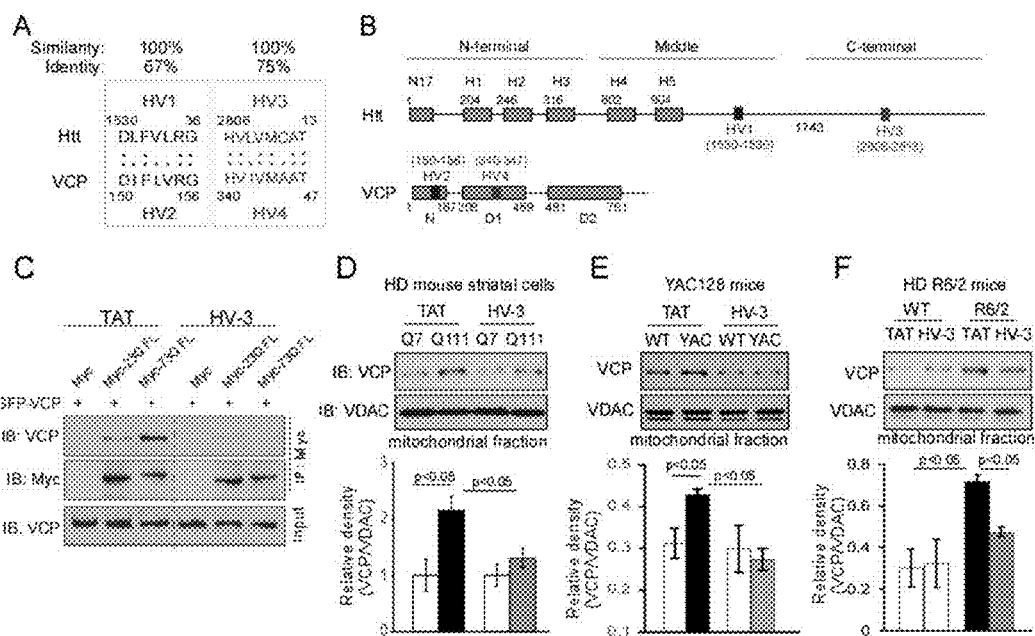

FIGS. 2(A-F) illustrate the development of a peptide blocker of Htt/VCP binding. (A) Sequence of homology between VCP (human, AAI21795) and Htt (human, NP_002102). Amino acids (SEQ ID NOs: 1-4) are represented by the one-letter code; stars (*) indicate identical amino acids; Columns (:) indicate high similarity between amino acids. Peptides HV1-4 correspond to these homologous regions. (B) Stick drawings of VCP and Htt main domains. Highlighted in the same colors are the two regions of homology between the two proteins, regions HV-1 and HV-3 in Htt and the corresponding regions HV-2 and HV-4 in VCP. (C) Mouse wild-type striatal cells were transfected with Myc control vector, Myc-full-length Htt with 23 Q or 73Q (Myc-23Q FL or Myc-73Q FL) and GFP-VCP for 48 hours following the treatment with peptide HV-3 or control peptide TAT (3 µM/day, each). The total lysates of cells were subjected to IP with anti-Myc antibodies followed by IB analysis with anti-VCP antibody. Shown are representative blots of three independent experiments. (D) HD mouse striatal cells were treated with the control peptide TAT or HV-3 (3 µM/day for 3 days). The shown blots are from three independent experiments. (E) YAC128 or wild-type mice were treated with control peptide TAT or peptide HV-3 (3 mg/kg/day) from the age of 3 months to 6 months. n=6 mice/group. (F) HD R6/2 mice or wild-type mice were treated with control peptide TAT or peptide HV-3 (3 mg/kg/day) from the age of 5 weeks to 9 weeks. n=6 mice/group. Mitochondrial fractions were isolated from cells or striata of mice. VCP mitochondrial levels were determined by western blot analysis. VDAC was used as a loading control. Data are mean±SE.

Figure 3:
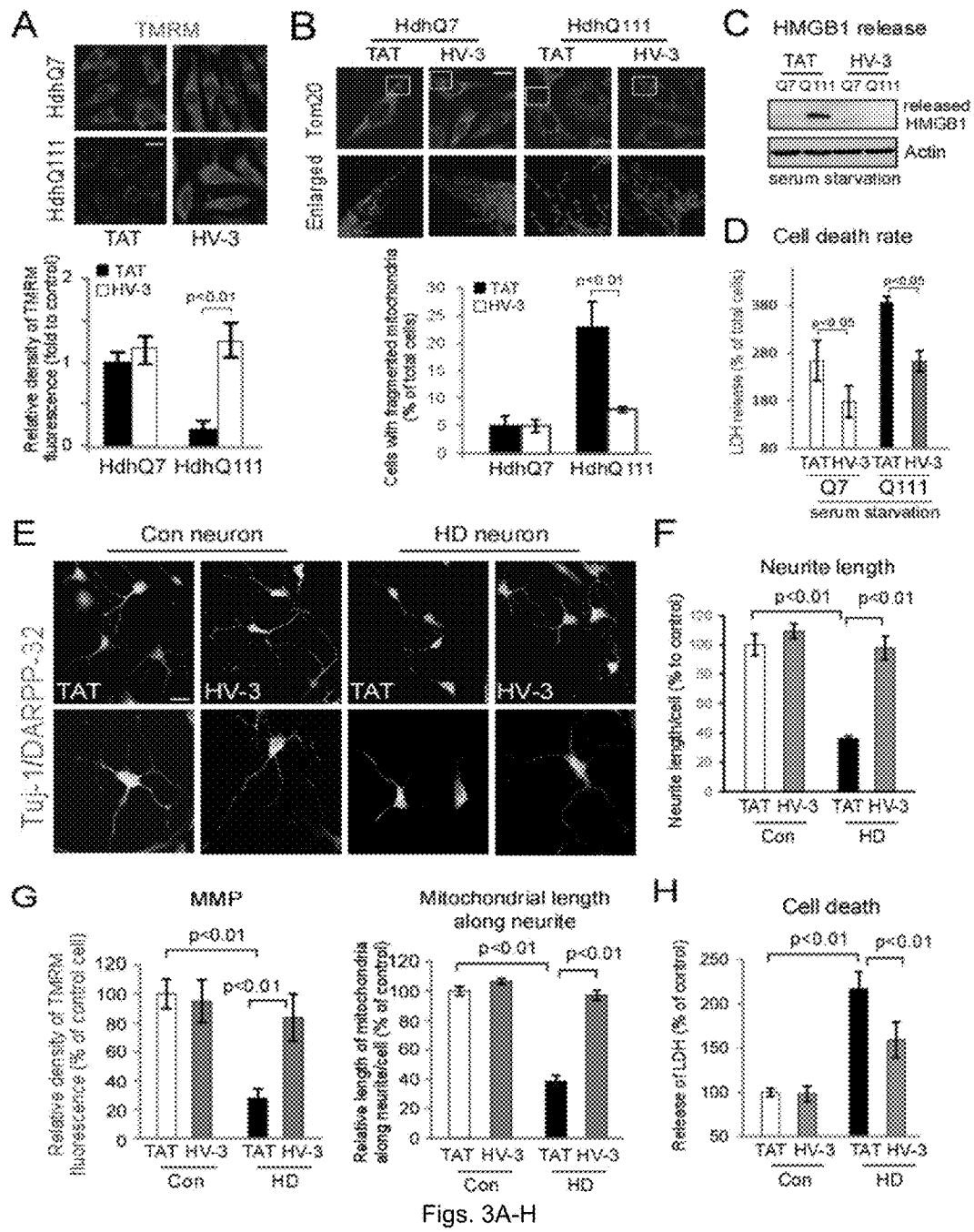

FIGS. 3(A-H) illustrate the peptide HV-3 treatment reduced mitochondrial damage and cell death in HD cell cultures. Mouse HdhQ7 and HdhQ111 striatal cells were treated with control peptide TAT or peptide HV-3 (3 µM/day for 3 days). (A) Mitochondrial membrane potential was determined by TMRM fluorescent dye. (B) Mitochondrial morphology was determined by staining cells with anti-Tom20 antibody. The percentage of cells with fragmented mitochondria relative to total number of cells was quantitated. For quantitation of imaging in above cells, at least 100 cells per group were counted by an observer blind to experimental conditions. (C) HD striatal cells were subjected to serum starvation for 24 hours. High-mobility group protein B1 (HMGB1) release into culture medium was determined by Western blot analysis with anti-HMGB1 antibody. (D) HD striatal cells were subjected to serum starvation for 24 hours. Cell death was determined by the release of lactate dehydrogenase (LDH). Control and HD patient-iPS cell derived neurons were treated with peptide HV-3 or control peptide TAT at 1 µM/day for 5 days starting 30 days after initiation of neuronal differentiation. (E) Left: Neurons were stained with anti-DARPP-32 and anti-Tuj-1 antibodies to indicate medium spiny neurons. Upper: a cluster of neurons; lower: individual neurons. (F) Quantitation of neurite length of medium spiny neurons. At least 50 neurons per group were counted by an observer blind to experimental conditions. (G) Left: Mitochondrial membrane potential was determined by TMRM fluorescent dye. Right: Mitochondria were stained by anti-Tom20 antibody. Mitochondrial length along neurites of DARPP-32-positive neurons was quantitated.

(H) Neuronal cell death induced by the withdrawal of the growth factor BDNF for 24 hours was determined by the release of LDH. All the Data are mean±SE from at least three independent studies. Scale bars: 10 µm.

Figure 4:
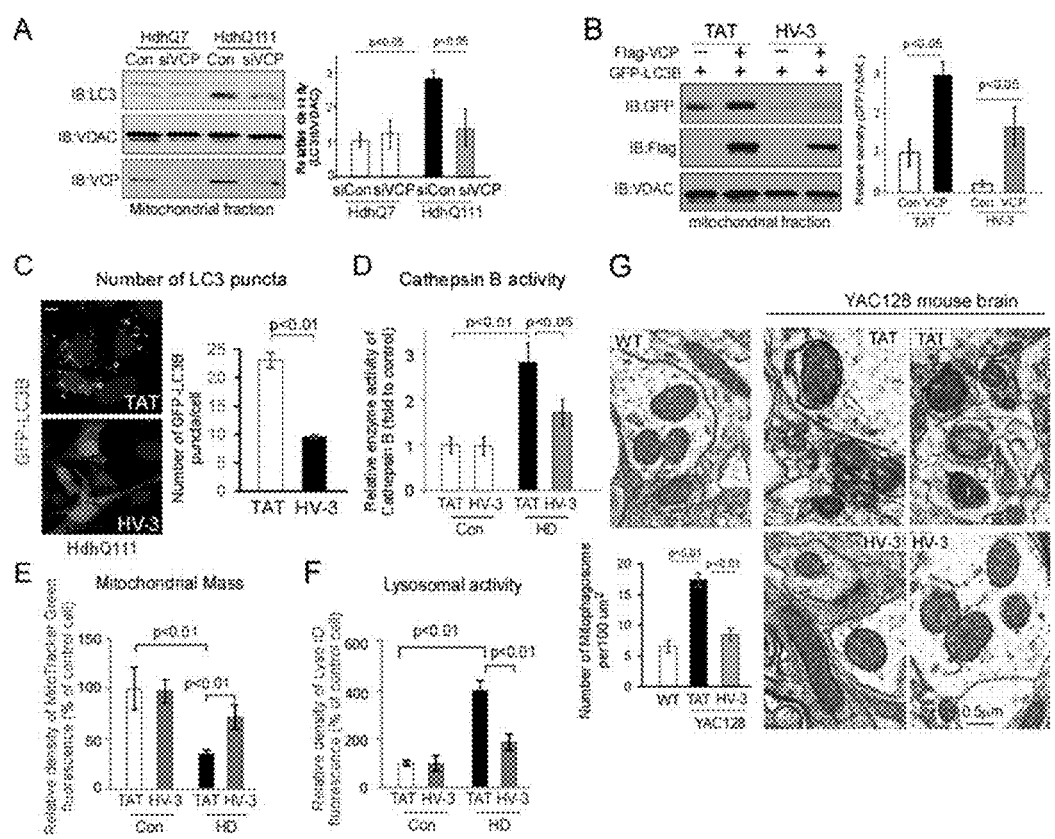

FIGS. 4(A-G) illustrate the treatment of HV-3 reduced excessive mitophagy in HD cell cultures and HD YAC128 mouse brains. (A) HdhQ7 and HdhQ111 cells were treated with control siRNA (con) or VCP siRNA (siVCP) for 48 hours. Mitochondria were isolated and LC3 mitochondrial levels were determined by Western blot. The quantitation of LC3II levels on mitochondria is provided on the right. VADC was used here as a loading control. (B) Flag-VCP and GFP-LC3B were co-transfected into HeLa cells. Mitochondria were isolated after 36 hours of transfection. The GFP-LC3B levels on mitochondria were examined by western blot analysis. VDAC was used as a loading control. Histogram: quantitation of GFP-LC3B mitochondrial protein level. HdhQ7 and HdhQ111 cells were treated with control peptide TAT or peptide HV-3 (3 µM/day for 3 days). (C) HdhQ111 cells were transfected with GFP-LC3B for 24 hours. The number of GFP-LC3B puncta was quantitated and shown in the histogram. Scale bars: 10 µm. (D) Enzyme activity of lysosomal cathepsin B was measured using a cathepsin B assay kit. Control and HD patient-iPS cell derived neurons were treated with peptide HV-3 or control peptide TAT at 1 µM/day for 5 days starting 30 days after neuronal differentiation. (E) Mitochondrial mass was measured by the fluorescent density of Mitotracker green. (F) Lysosomal activity was examined by staining neurons with Lyso-ID Red dye. Scale bars: 10 µm. (G) YAC128 mice and wildtype mice were treated with control peptide TAT or peptide HV-3 (3 mg/kg/day) from the age of 3 months to 9 months. Transmission electron microscope images of striata from 9-month-old wild-type mice and YAC128 mice was performed. Arrows indicate mitophagosomes. Histogram: the number of mitophagosomes per 100 $\mu m^2$ was counted and quantitated. Fifteen random areas in the striatum in each animal were analyzed. All the data are mean±SE of three independent experiments.

Figure 5:
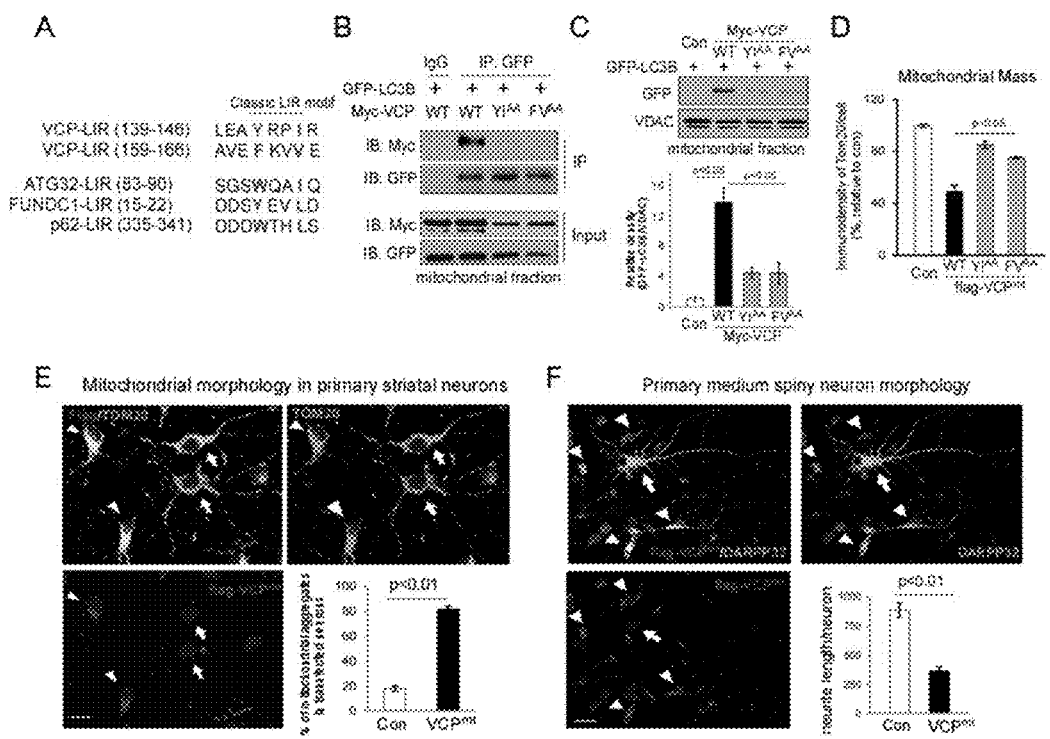

FIGS. 5(A-F) illustrate: VCP caused excessive mitophagy by binding to LC3.

(A) Putative LIR sequences in VCP were aligned manually for comparison with the classical LIR motifs of ATG32, FUNDC1 and p62. The amino acids in blue indicate the conserved core residues of LIR. (B) GFP-LC3B was co-expressed with the indicated plasmids in HeLa cells. Mitochondrial lysates were subjected to immunoprecipitation (IP) with anti-GFP antibody, and immunoprecipitates were analyzed by immunoblotting (IB) with anti-Myc and anti-GFP antibodies. Representative blots are from 3 independent experiments. (C) GFP-LC3B was co-transfected with the indicated plasmids in HeLa cells. Mitochondria were isolated and GFP-LC3B mitochondrial protein levels were determined by Western blot. Data are mean±SE from 4 independent studies. (D) HeLa cells were transfected with the indicated plasmids. Mitochondria were stained with an anti-Tom20 antibody. Mitochondrial mass was determined by quantitating fluorescent density of Tom20 immunostaining. At least 100 cells per group were counted by an observer blind to experimental conditions. Data are mean±SE from 3 independent studies. Primary rat striatal neurons (DIV 7) were transfected with flag-VCPmt plasmids for 3 days. (E) Neurons were stained with anti-Tom20 (green) and anti-flag (red) antibodies. Mitochondrial morphology was examined by microscopy.

(F) Medium spiny neurons were labeled with anti-DARPP-32 (green). Neuronal morphology was imaged and the neurite length of medium spiny neurons was quantitated. At least 50 neurons per group were counted by an observer blind to experimental conditions. Scale bars: 10 µm. All the data are mean±SE from 3 independent experiments.

Figure 6:
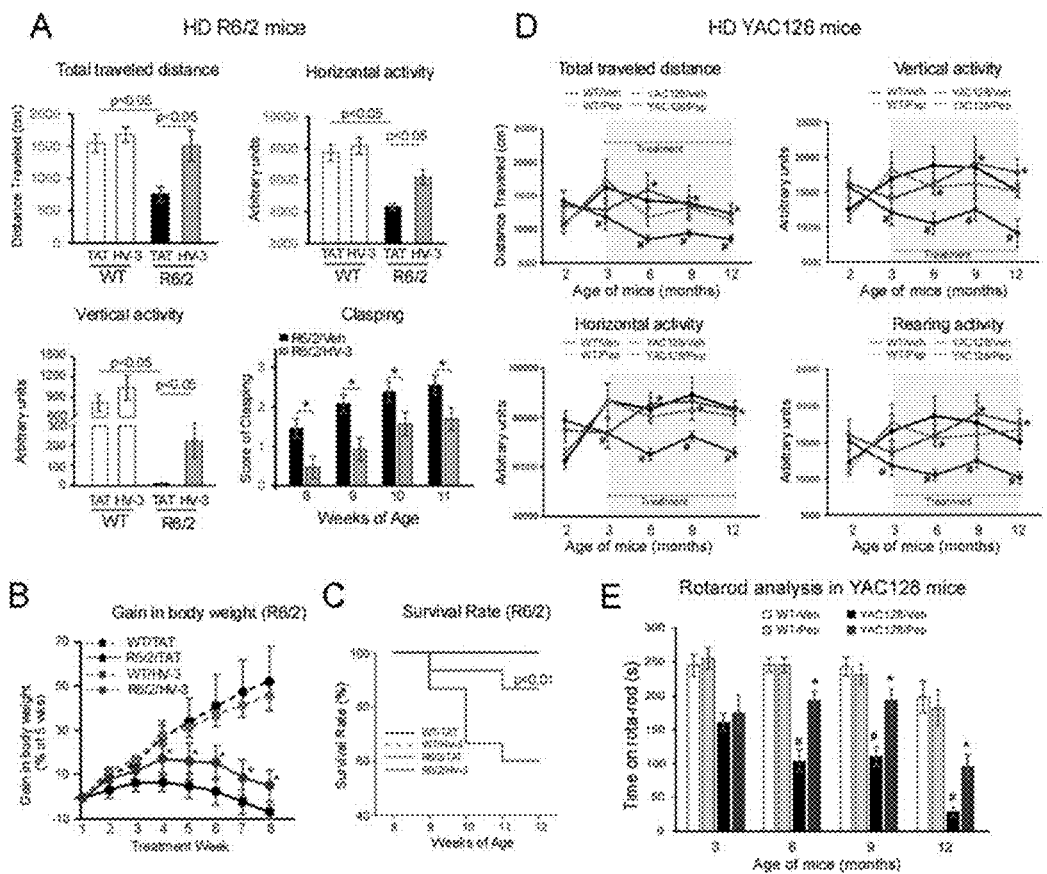

FIGS. 6(A-E) illustrate: HV-3 treatment reduced motor deficits in both R6/2 and YAC128 HD mice. HD R6/2 mice and wild-type littermates were treated with either the control peptide or peptide HV-3 (at 3 mg/kg/day, subcutaneous administration with an Alzet osmotic pump) from 5 to 13 weeks of age. (A) One hour of overall movement activity in R6/2 mice and wildtype littermates (total traveled distance, horizontal and vertical activities) was determined by locomotion activity chamber at the age of 13 weeks (n=15 mice/group). Hindlimb clasping was assessed with the tail suspension test once a week from the ages of 8 to 11 weeks (n=15 mice/group). *, $p<0.05$. Body weight (B) and survival (C) were recorded from the age of 5 weeks to 13 weeks (n=15 mice/group). *, $p<0.05$ vs. HD mice treated with control peptide TAT; repeated-measures two-way ANOVA. YAC128 mice and wild-type littermates were treated with the control peptide TAT or HV-3 peptides from the age of 3 months to the age of 12 months. Mouse behavioral and HD-associated pathology were determined every three months after beginning treatment. (D) 24 hours of general motility of YAC128 mice and wildtype littermates was monitored by a locomotion activity chamber at the indicated age (n=15-20 mice/group). #, p<0.05 vs. wild-type mice treated with control peptide TAT; *, p<0.05 vs. HD mice treated with control peptide TAT. (E) Rotarod performance of YAC128 and wildtype mice was evaluated at the indicated age (n=15-20 mice/group). #, p<0.05 vs. wild-type mice treated with control peptide TAT; *, p<0.05 vs. HD mice treated with control peptide TAT. All data are expressed as mean±SE.

Figure 7:
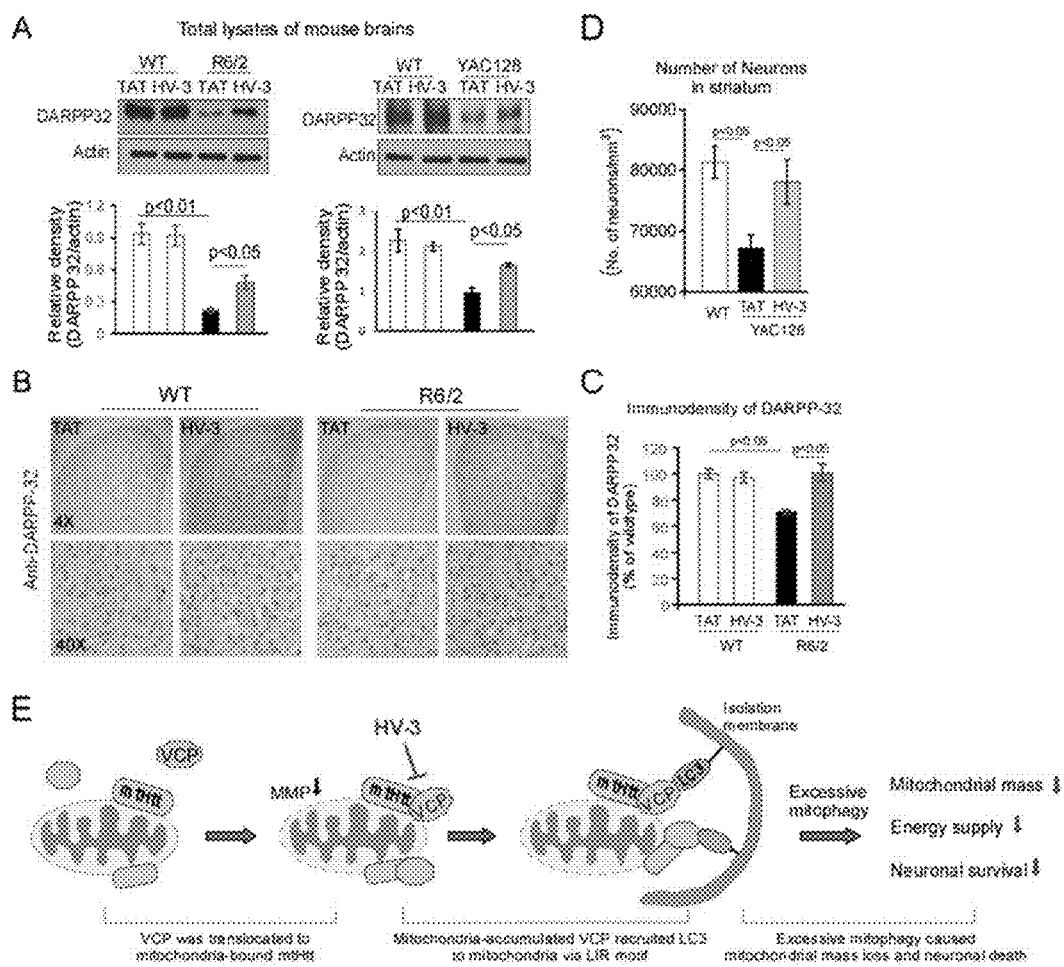

FIGS. 7(A-E) illustrate: HV-3 treatment reduced mitochondrial defects and neuropathology in HD mice. (A) DARPP-32 protein levels were determined by Western blot of R6/2 (left) and YAC128 (right) mouse striatal extracts. Upper: representative immunoblotting (IB); Lower: histogram of quantification of DARPP-32 levels. Actin was used as a loading control. Data are mean±SE of 6 mice/group. (B) Photomicrographs of DARPP-32 immunostaining were obtained from the dorsolateral striatum of TAT- or HV-3-treated R6/2 mice. (C) Quantitation of DARPP-32 immunodensity. Data are mean±SE of 6 mice. (D) Quantitation of NeuN-immunopositive cells in the dorsolateral striatum. Data are mean±SE of 6 mice. (E) A summary scheme. VCP is selectively recruited to the mitochondria by interacting with mitochondria-bound mtHtt. Mitochondria-accumulated VCP acts as a mitophagic adaptor to bind to the autophagosome component LC3 via an LC3 interacting region (LIR motif). As a result, mtHtt-induced VCP association with mitochondria causes excessive mitophagy which results in mitochondrial mass loss, mitochondrial dysfunction and neuronal cell death. Blocking mtHtt to VCP binding on mitochondria by a selective peptide HV-3 inhibits VCP mitochondrial accumulation, which reduces excessive mitophagy and subsequent neuronal degeneration. Consequently, treatment with HV-3 both in HD cultures and in HD animals reduces HD-associated neuropathology.

Figure 8:
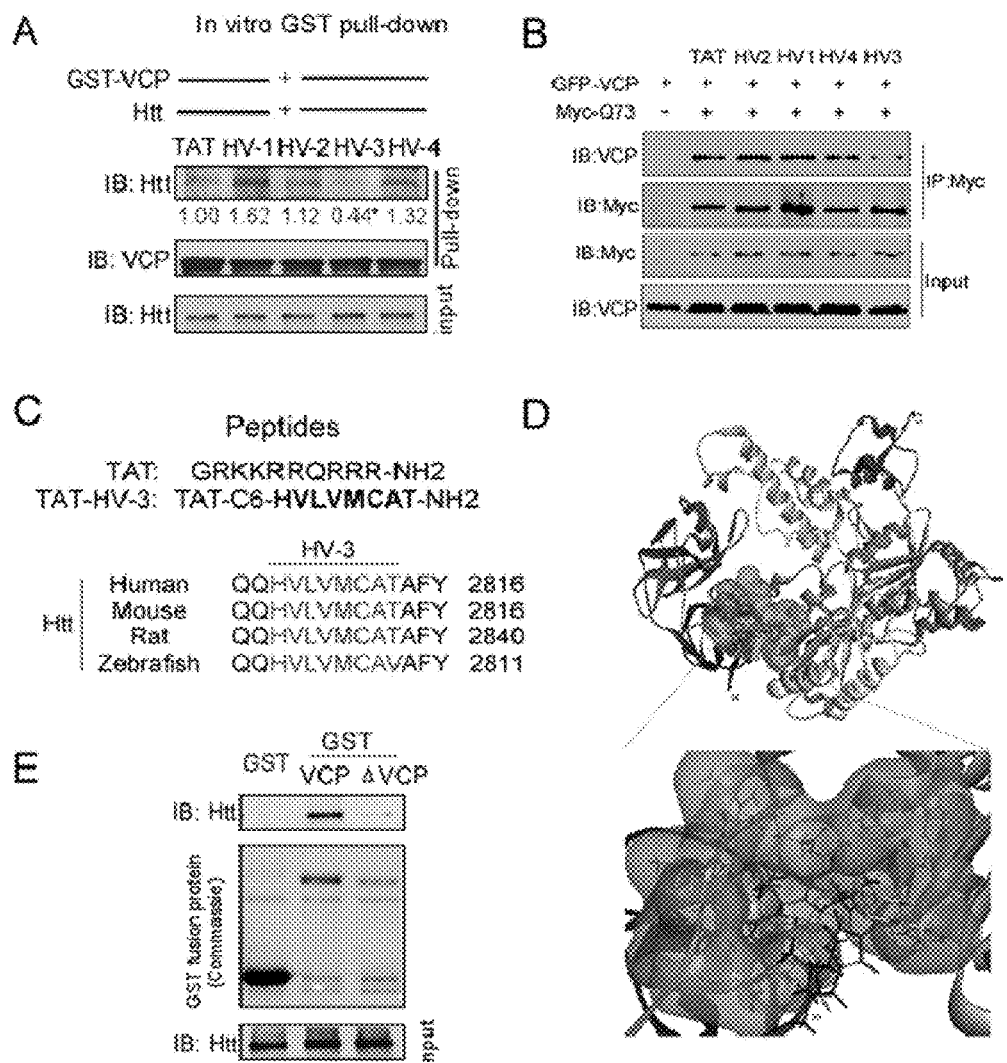

FIGS. 8(A-E) illustrate: GST or GST-VCP was incubated with total lysates of mouse brain and the indicated peptides (3 µM) for 16 hours, followed by immunoblotting with anti-Htt antibodies. Representative blots are from three independent experiments. Quantitation of VCP/Htt binding was shown below the blot as Mean of three independent experiments. *, p<0.05 vs. TAT-treated group. (B) HEK293 cells were co-expressed GFP-VCP and Myc-73Q FL plasmids as indicated. After 48 hours incubation with the indicated peptides (3 µM/day, each), immunoprecipitation analysis was performed. The shown blots are from three independent experiments. (C) Upper: sequence of the HV-3 peptide and control peptide TAT. Lower: HV-3 peptide sequence is highly conserved among species. (D) The HV-3 peptide was docked to the VCP. Upper: Cartoon representing the predicted VCP structure using the mouse crystal structure of p97 (PDB ID 3CF1); sticks represent the structure of HV-3. Lower: the enlarged area. (E) The sequence in VCP corresponding to HV-3 in Htt was deleted (ΔVCP). GST, GST-VCP, or GST-ΔVCP was incubated with total lysates of mouse brain for 16 hours followed by immunoblotting (IB) with anti-Htt antibodies.

Figure 9:
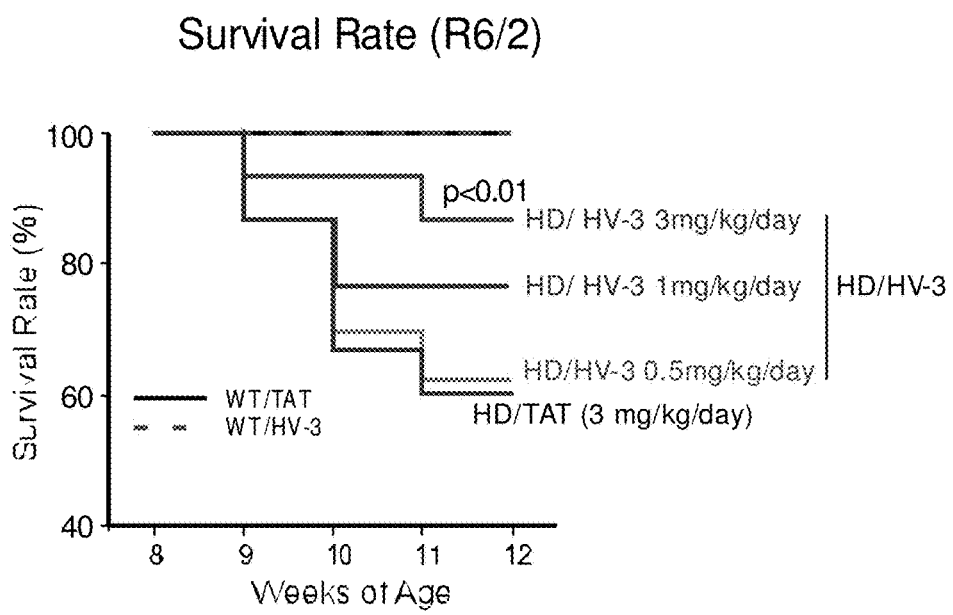

FIG. 9 illustrates plots showing HV-3 dose response in animal models of R6/2 mice.

DETAILED DESCRIPTION

The embodiments described herein are not limited to the particular methodology, protocols, and reagents, etc., and as such may vary. The terminology used herein is for the purpose of describing particular embodiments only, and is not intended to limit the scope of the present invention, which is defined solely by the claims. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

As used herein, "one or more of a, b, and c" means a, b, c, ab, ac, bc, or abc. The use of "or" herein is the inclusive or.

The term "administering" to a patient includes dispensing, delivering or applying an active compound in a pharmaceutical formulation to a subject by any suitable route for delivery of the active compound to the desired location in the subject (e.g., to thereby contact a desired cell such as a desired neuron), including administration into the cerebrospinal fluid or across the blood-brain barrier, delivery by either the parenteral or oral route, intramuscular injection, subcutaneous or intradermal injection, intravenous injection, buccal administration, transdermal delivery and administration by the rectal, colonic, vaginal, intranasal or respiratory tract route. The agents may, for example, be administered to a comatose, anesthetized or paralyzed subject via an intravenous injection or may be administered intravenously to a pregnant subject to stimulate axonal growth in a fetus. Specific routes of administration may include topical application (such as by eyedrops, creams or erodible formulations to be placed under the eyelid, intraocular injection into the aqueous or the vitreous humor, injection into the external layers of the eye, such as via subconjunctival injection or subtenon injection, parenteral administration or via oral routes.

The term "antibody", includes human and animal mAbs, and preparations of polyclonal antibodies, synthetic antibodies, including recombinant antibodies (antisera), chimeric antibodies, including humanized antibodies, anti-idiotopic antibodies and derivatives thereof. A portion or fragment of an antibody refers to a region of an antibody that retains at least part of its ability (binding specificity and affinity) to bind to a specified epitope. The term "epitope" or "antigenic determinant" refers to a site on an antigen to which antibody paratope binds. Epitopes formed from contiguous amino acids are typically retained on exposure to denaturing solvents whereas epitopes formed by tertiary folding are typically lost on treatment with denaturing solvents. An epitope typically includes at least 3, at least 5, or 8 to 10, or about 13 to 15 amino acids in a unique spatial conformation. Methods of determining spatial conformation of epitopes include, for example, x-ray crystallography and 2-dimensional nuclear magnetic resonance.

The terms "chimeric protein" or "fusion protein" refer to a fusion of a first amino acid sequence encoding a polypeptide with a second amino acid sequence defining a domain (e.g., polypeptide portion) foreign to and not substantially homologous with the domain of the first polypeptide. A chimeric protein may present a foreign domain, which is found (albeit in a different protein) in an organism, which also expresses the first protein, or it may be an "interspecies", "intergenic", etc. fusion of protein structures expressed by different kinds of organisms.

The term "contacting nerves", "contacting neurons", "treating nerves", or "treating neurons" refers to any mode of agent delivery or "administration," either to cells or to whole organisms, in which the agent is capable of exhibiting its pharmacological effect in neurons. "Contacting neurons" includes both in vivo and in vitro methods of bringing an agent of the invention into proximity with a neuron. Suitable modes of administration can be determined by those skilled in the art and such modes of administration may vary between agents.

An "effective amount" of an agent or therapeutic peptide is an amount sufficient to achieve a desired therapeutic or pharmacological effect, such as an amount that is capable of activating the growth of neurons. An effective amount of an agent as defined herein may vary according to factors such as the disease state, age, and weight of the subject, and the ability of the agent to elicit a desired response in the subject. Dosage regimens may be adjusted to provide the optimum therapeutic response. An effective amount is also one in which any toxic or detrimental effects of the active compound are outweighed by the therapeutically beneficial effects.

The term "expression" refers to the process by which nucleic acid is translated into peptides or is transcribed into RNA, which, for example, can be translated into peptides, polypeptides or proteins. If the nucleic acid is derived from genomic DNA, expression may, if an appropriate eukaryotic host cell or organism is selected, include splicing of the mRNA. For heterologous nucleic acid to be expressed in a host cell, it must initially be delivered into the cell and then, once in the cell, ultimately reside in the nucleus.

The term "genetic therapy" involves the transfer of heterologous DNA to cells of a mammal, particularly a human, with a disorder or conditions for which therapy or diagnosis is sought. The DNA is introduced into the selected target cells in a manner such that the heterologous DNA is expressed and a therapeutic product encoded thereby is produced. Alternatively, the heterologous DNA may in some manner mediate expression of DNA that encodes the therapeutic product; it may encode a product, such as a peptide or RNA that in some manner mediates, directly or indirectly, expression of a therapeutic product. Genetic therapy may also be used to deliver nucleic acid encoding a gene product to replace a defective gene or supplement a gene product produced by the mammal or the cell in which it is introduced. The introduced nucleic acid may encode a therapeutic compound, such as a growth factor inhibitor thereof, or a tumor necrosis factor or inhibitor thereof, such as a receptor therefore, that is not normally produced in the mammalian host or that is not produced in therapeutically effective amounts or at a therapeutically useful time. The heterologous DNA encoding the therapeutic product may be modified prior to introduction into the cells of the afflicted host in order to enhance or otherwise alter the product or expression thereof.

The term "gene" or "recombinant gene" refers to a nucleic acid comprising an open reading frame encoding a polypeptide, including both exon and (optionally) intron sequences.

The term "heterologous nucleic acid sequence" is typically DNA that encodes RNA and proteins that are not normally produced in vivo by the cell in which it is expressed or that mediates or encodes mediators that alter expression of endogenous DNA by affecting transcription, translation, or other regulatable biochemical processes. A heterologous nucleic acid sequence may also be referred to as foreign DNA. Any DNA that one of skill in the art would recognize or consider as heterologous or foreign to the cell in which it is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

The terms "homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into a target tissue, such that it enters the animal's system and, thus, is subject to metabolism and other like processes, for example, subcutaneous administration.

The term "patient" or "subject" or "animal" or "host" refers to any mammal. The subject may be a human, but can also be a mammal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

The terms "polynucleotide sequence" and "nucleotide sequence" are also used interchangeably herein.

The terms "peptide" or "polypeptide" are used interchangeably herein and refer to compounds consisting of from about 2 to about 90 amino acid residues, inclusive, wherein the amino group of one amino acid is linked to the carboxyl group of another amino acid by a peptide bond. A peptide can be, for example, derived or removed from a native protein by enzymatic or chemical cleavage, or can be prepared using conventional peptide synthesis techniques (e.g., solid phase synthesis) or molecular biology techniques (see Sambrook et al., MOLECULAR CLONING: LAB. MANUAL (Cold Spring Harbor Press, Cold Spring Harbor, N.Y., 1989)). A "peptide" can comprise any suitable L- and/or D-amino acid, for example, common a-amino acids (e.g., alanine, glycine, valine), non-a-amino acids (e.g., P-alanine, 4-aminobutyric acid, 6aminocaproic acid, sarcosine, statine), and unusual amino acids (e.g., citrulline, homocitruline, homoserine, norleucine, norvaline, ornithine) The amino, carboxyl and/or other functional groups on a peptide can be free (e.g., unmodified) or protected with a suitable protecting group. Suitable protecting groups for amino and carboxyl groups, and means for adding or removing protecting groups are known in the art. See, e.g., Green & Wuts, PROTECTING GROUPS IN ORGANIC SYNTHESIS (John Wiley & Sons, 1991). The functional groups of a peptide can also be derivatized (e.g., alkylated) using art-known methods.

The term "peptidomimetic", refers to a protein-like molecule designed to mimic a peptide. Peptidomimetics typically arise either from modification of an existing peptide, or by designing similar systems that mimic peptides, such as peptoids and β-peptides. Irrespective of the approach, the altered chemical structure is designed to advantageously adjust the molecular properties such as, stability or biological activity. These modifications involve changes to the peptide that do not occur naturally (such as altered backbones and the incorporation of nonnatural amino acids).

The terms "prevent" or "preventing" refer to reducing the frequency or severity of a disease or condition. The term does not require an absolute preclusion of the disease or condition. Rather, this term includes decreasing the chance for disease occurrence.

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

The term "recombinant," as used herein, means that a protein is derived from a prokaryotic or eukaryotic expression system.

The term "therapeutically effective" means that the amount of the composition used is of sufficient quantity to ameliorate one or more causes, symptoms, or sequelae of a disease or disorder. Such amelioration only requires a reduction or alteration, not necessarily elimination, of the causes, symptoms, or sequelae of a disease or disorder.

The term "tissue-specific promoter" means a nucleic acid sequence that serves as a promoter, i.e., regulates expression of a selected nucleic acid sequence operably linked to the promoter, and which affects expression of the selected nucleic acid sequence in specific cells of a tissue, such as cells of epithelial cells. The term also covers so-called "leaky" promoters, which regulate expression of a selected nucleic acid primarily in one tissue, but cause expression in other tissues as well. The term "transfection" is used to refer to the uptake of foreign DNA by a cell. A cell has been "transfected" when exogenous DNA has been introduced inside the cell membrane. A number of transfection techniques are generally known in the art. See, e.g., Graham et al., Virology 52:456 (1973); Sambrook et al., Molecular Cloning: A Laboratory Manual (1989); Davis et al., Basic Methods in Molecular Biology (1986); Chu et al., Gene 13:197 (1981). Such techniques can be used to introduce one or more exogenous DNA moieties, such as a nucleotide integration vector and other nucleic acid molecules, into suitable host cells. The term captures chemical, electrical, and viral-mediated transfection procedures.

The terms "transcriptional regulatory sequence" is a generic term used throughout the specification to refer to nucleic acid sequences, such as initiation signals, enhancers, and promoters, which induce or control transcription of protein coding sequences with which they are operably linked. In some examples, transcription of a recombinant gene is under the control of a promoter sequence (or other transcriptional regulatory sequence), which controls the expression of the recombinant gene in a cell-type in which expression is intended. It will also be understood that the recombinant gene can be under the control of transcriptional regulatory sequences which are the same or which are different from those sequences, which control transcription of the naturally occurring form of a protein.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "vector" refers to a nucleic acid molecule capable of transporting another nucleic acid to which it has been linked. Preferred vectors are those capable of one or more of, autonomous replication and expression of nucleic acids to which they are linked. Vectors capable of directing the expression of genes to which they are operatively linked are referred to herein as "expression vectors".

The term "wild type" refers to the naturally-occurring polynucleotide sequence encoding a protein, or a portion thereof, or protein sequence, or portion thereof, respectively, as it normally exists in vivo. As used herein, the term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The agents, compounds, compositions, antibodies, etc. used in the methods described herein are considered to be purified and/or isolated prior to their use. Purified materials are typically "substantially pure", meaning that a nucleic acid, polypeptide or fragment thereof, or other molecule has been separated from the components that naturally accompany it. Typically, the polypeptide is substantially pure when it is at least 60%, 70%, 80%, 90%, 95%, or even 99%, by weight, free from the proteins and other organic molecules with which it is associated naturally. For example, a substantially pure polypeptide may be obtained by extraction from a natural source, by expression of a recombinant nucleic acid in a cell that does not normally express that protein, or by chemical synthesis. "Isolated materials" have been removed from their natural location and environment. In the case of an isolated or purified domain or protein fragment, the domain or fragment is substantially free from amino acid sequences that flank the protein in the naturally-occurring sequence. The term "isolated DNA" means DNA has been substantially freed of the genes that flank the given DNA in the naturally occurring genome. Thus, the term "isolated DNA" encompasses, for example, cDNA, cloned genomic DNA, and synthetic DNA.

The terms "portion", "fragment", "variant", "derivative" and "analog", when referring to a polypeptide include any polypeptide that retains at least some biological activity referred to herein (e.g., inhibition of an interaction such as binding). Polypeptides as described herein may include portion, fragment, variant, or derivative molecules without limitation, as long as the polypeptide still serves its function. Polypeptides or portions thereof of the present invention may include proteolytic fragments, deletion fragments and in particular, or fragments that more easily reach the site of action when delivered to an animal.

Embodiments described herein relate to compositions and methods for inhibiting aberrant Valosin-Containing Protein (VCP) accumulation in the mitochondria, and particularly relates to compositions and methods for treating disease or disorders associated with aberrant VCP accumulation in the mitochondria of nerve cells.

VCP, also known as p97 in vertebrates and Cdc48 in *S. cerevisiae*, is a class II member of the ATPase associated with diverse cellular activities. VCP is highly conserved from archaebacteria to humans, and is located in different subcellular organelles, including the endoplasmic reticulum (ER), mitochondria, and nucleus, where it functions in diverse cellular processes including ER-associated protein degradation (ERAD), mitochondria-associated degradation (MAD), autophagy, and DNA repair. VCP can translocate to mitochondria, where it is required for turnover of mitochondrial outer membrane protein Mitofusins and parkin-dependent mitophagy. Overexpression of VCP results in mitochondrial fragmentation and cell death in neurons exposed to various mitochondrial toxins, such as rotenone, 6-OHDA, Aβ-peptides. Pathogenic mutations in the VCP in yeast and Drosophila cause mitochondrial depolarization, mitochondrial oxidative stress, reduced ATP production, and mitochondrial aggregations. Mice with VCP mutants displayed degeneration of mitochondria, enhanced autophagy, motor neuron degeneration, and early lethality. Mutations of VCP gene in humans cause frontotemporal dementia, amyotrophic lateral sclerosis (ALS), and muscular and bone degeneration, all of which are manifestations of mitochondrial dysfunction.

VCP was found to be involved in the pathogenesis of polyglutamine (polyQ) diseases. First, endogenous VCP was found to co-localize with polyglutamine-containing aggregates that were found in patients with HD and Machado-Joseph disease. Second, VCP can directly bind to multiple polyglutamine disease proteins, including huntingtin, ataxin-1, ataxin-7, and androgen receptors. Third, in a transgenic Drosophila model expressing a fragments of polyQ gene carrying either 79 or 92 CAG repeats, an up-regulation of VCP expression was observed prior to cell death, and over-expression of VCP severely enhanced eye degeneration. Thus, VCP can act as a cell death effector in polyQ-induced neurodegeneration.

VCP was found to be aberrantly recruited to mitochondria via mitochondria-bound mutant huntingtin protein (mHtt) protein-protein interaction. Wild-type huntingtin protein (Htt) can serve as a scaffold protein that regulates various physiological processes through protein-protein interactions. VCP was found to bind to mtHtt in HD brains, and endogenous VCP can co-localize with mtHtt aggregates in the cytoplasm in primary neurons expressing a fragment of mtHtt. Such accumulation of VCP on mitochondria resulted in excessive mitophagy, mitochondrial mass loss, and subsequent neuronal degeneration in HD models in culture and in animals.

It was found that blocking VCP translocation to mitochondria by inhibiting VCP/mtHtt protein interactions inhibited VCP-mediated mitophagy impairment, suppressed mitochondrial dysfunction, and reduced HD-associated neuropathology and motor deficits in two HD transgenic mouse models and thus can be used to treat neurodegneration associated with aberrant accumulation of VCP in the mitochondria. Indeed, in vitro and in vivo data described herein shows that blocking VCP/mtHtt binding abolished VCP translocation to the mitochondria and reduced mitochondrial damage, further emphasizing that the binding of VCP/mtHtt is required for VCP relocation to the mitochondria. Significantly, inhibition of VCP/mtHtt binding reduced HD-related behavioral and pathological phenotypes in two HD transgenic mice. Thus, the formation of aberrant complex of VCP/mtHtt on the mitochondria is a key step in initiating mitochondrial injury, which in turn results in neuronal pathology in HD Inhibitors that selectively block VCP mitochondrial accumulation can provide a therapeutic route for HD and multiple polyglutamine (polyQ) diseases in which the binding of VCP with mutant polyQ proteins and associated mitochondrial defects are characterized.

Accordingly, therapeutic agents that inhibit aberrant VCP accumulation in the mitochondria by polyQ proteins can be use in methods of treating polyQ mediated neurodegeneration and/or neurodegenerative diseases in a subject in need thereof. The polyQ mediated neurodegeneration and/or neurodegenerative diseases can include, for example, Huntington's disease, spinocerebellar ataxias of types 1, 2, 3, 6, 7 and 17, dentatorubral pallidoluysian atrophy as well as spinobulbar muscular atrophy (Kennedy syndrome).

Other neudegenerative diseases that can also be treated by therapeutic agents that inhibit aberrant VCP accumulation in the mitochondria can include Parkinson's disease, Multiple Sclerosis (MS), Amyotrophic Lateral Sclerosis (ALS), multi-system atrophy, Alzheimer's disease, stroke, Spinal-cerebellar ataxia, progressive supranuclear palsy, progressive supernuclear palsy, granulovacuolar disease, frontotemporal dementia, corticobasal degeneration, epilepsy, autoimmune encephalomyelitis, diabetic neuropathy, glaucomatous neuropathy, Pick's disease, Lewy Body disease, Creutzfeld-Jacob Disease (CJD), variant Creutzfeld-Jacob Disease, new variant Creutzfeld-Jacob Disease, or kuru disease.

In some embodiments, a therapeutic agent that inhibits or reduces aberrant VCP accumulation in the mitochondria by polyQ proteins, can include a therapeutic peptide or small molecule that binds to and/or complexes with VCP to inhibit the binding or complexing of VCP and the polyQ protein, such as mtHtt. Accordingly, therapeutic peptides or small molecules that bind to and/or complex with VCP to inhibit or reduce binding or complexing of VCP and the polyQ protein as well as inhibit aberrant VCP accumulation in the mitochondria can be used to treat neurodegerative diseases or disorders, such as Huntington's disease, in a subject in need thereof.

In some embodiments, the therapeutic agent can comprise a short peptide derived from interaction sites between VCP and the polyQ protein that inhibits or reduces binding or complexing of VCP and the polyQ protein. For example, the therapeutic agent can comprise short peptides of VCP or mtHtt that can inhibit the interaction of VCP and mtHtt. In one embodiment, the therapeutic agent can comprise a short peptide that is derived from Htt and represents a sequence homologous to VCP. The therapeutic peptide can have at least about 75% sequence identity to about 8 to about 10 consecutive amino acids of an interaction site of VCP with the polyglutamine protein. In some embodiments, the therapeutic peptide can have an amino acid sequence that is at least about 75% identical to SEQ ID NO: 4. For example, the therapeutic peptide can have an amino acid sequence of SEQ ID NO: 3. A short peptide having the amino acid of SEQ ID NO: 3 is referred herein as HV-3. HV-3 was found to block the binding of VCP to mtHtt in cultures and in animal models of HD, which shows that HV-3 can compete with Htt binding to VCP and/or that it can prevent the exposure of the VCP-binding site on Htt.

In some embodiments, the therapeutic agent or therapeutic peptide can include, a peptide that consists essentially, and/or consists of about 8 to about 12 amino acids and has an amino acid sequence that is at least about 65%, at least about 70%, at least about 75%, at least about 80%, at least about 85%, at least about 90%, at least about 95%, or about 100% homologous to an about 6 to about 12 consecutive amino acids (e.g., about 8 to about 10 consecutive amino acids) of an interaction site of VCP and polyQ protein, such as a petide having the amino acid sequence of SEQ ID NO: 3 or SEQ ID NO: 4.

The therapeutic peptides described herein can be subject to other various changes, substitutions, insertions, and deletions where such changes provide for certain advantages in its use. In this regard, therapeutic peptides that bind to and/or complex with an interaction site of VCP and a polyQ protein can correspond to or be substantially homologous with, rather than be identical to, the sequence of a recited polypeptide where one or more changes are made and it retains the ability to inhibits or reduces interaction of VCP and a polyQ protein to inhibit aberrant VCP accumulation in the mitochondrial of a cell, such as a neuron.

The therapeutic peptide can be in any of a variety of forms of polypeptide derivatives that include amides, conjugates with proteins, cyclized polypeptides, polymerized polypeptides, analogs, fragments, chemically modified polypeptides and the like derivatives.

It will be appreciated that the conservative substitution can also include the use of a chemically derivatized residue in place of a non-derivatized residue provided that such peptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those polypeptides, which contain one or more naturally occurring amino acid derivatives of the twenty standard amino acids. For examples:

4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides described herein also include any polypeptide having one or more additions and/or deletions or residues relative to the sequence of a polypeptide whose sequence is shown herein, so long as the requisite activity is maintained.

One or more of peptides of the therapeutic peptides described herein can also be modified by natural processes, such as posttranslational processing, and/or by chemical modification techniques, which are known in the art. Modifications may occur in the peptide including the peptide backbone, the amino acid side-chains and the amino or carboxy termini. It will be appreciated that the same type of modification may be present in the same or varying degrees at several sites in a given peptide. Modifications comprise for example, without limitation, acetylation, acylation, addition of acetomidomethyl (Acm) group, ADP-ribosylation, amidation, covalent attachment to fiavin, covalent attachment to a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination (for reference see, Protein-structure and molecular properties, 2nd Ed., T. E. Creighton, W. H. Freeman and Company, New-York, 1993).

Peptides and/or proteins described herein may also include, for example, biologically active mutants, variants, fragments, chimeras, and analogues; fragments encompass amino acid sequences having truncations of one or more amino acids, wherein the truncation may originate from the amino terminus (N-terminus), carboxy terminus (C-terminus), or from the interior of the protein. Analogues of the invention involve an insertion or a substitution of one or more amino acids. Variants, mutants, fragments, chimeras and analogues may function as inhibitors of the interaction of VCP and polyQ proteins (without being restricted to the present examples).

The therapeutic peptides described herein may be prepared by methods known to those skilled in the art. The peptides and/or proteins may be prepared using recombinant DNA. For example, one preparation can include cultivating a host cell (bacterial or eukaryotic) under conditions, which provide for the expression of peptides and/or proteins within the cell.

The purification of the polypeptides may be done by affinity methods, ion exchange chromatography, size exclusion chromatography, hydrophobicity or other purification technique typically used for protein purification. The purification step can be performed under non-denaturating conditions. On the other hand, if a denaturating step is required, the protein may be renatured using techniques known in the art.

In some embodiments, the therapeutic peptides described herein can include additional residues that may be added at either terminus of a polypeptide for the purpose of providing a "linker" by which the polypeptides can be conveniently linked and/or affixed to other polypeptides, proteins, detectable moieties, labels, solid matrices, or carriers.

Amino acid residue linkers are usually at least one residue and can be 40 or more residues, more often 1 to 10 residues. Typical amino acid residues used for linking are glycine, tyrosine, cysteine, lysine, glutamic and aspartic acid, or the like. In addition, a subject polypeptide can differ by the sequence being modified by terminal-NH2 acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

In some embodiments, the linker can be a flexible peptide linker that links the therapeutic peptide to other polypeptides, proteins, and/or molecules, such as detectable moieties, labels, solid matrices, or carriers. A flexible peptide linker can be about 20 or fewer amino acids in length. For example, a peptide linker can contain about 12 or fewer amino acid residues, e.g., 3, 4, 5, 6, 7, 8, 9, 10, 11, and 12. In some cases, a peptide linker comprises two or more of the following amino acids: glycine, serine, alanine, and threonine.

In some embodiments, a therapeutic agent comprising the therapeutic peptides described herein can be provided in the form of a conjugate protein or drug delivery construct includes at least a transport subdomain(s) or moiety(ies) (i.e., transport moieties or cell penetrating moieties) that is linked to the therapeutic peptide. The transport moieties can facilitate uptake of the therapeutic polypeptides into a mammalian (i.e., human or animal) tissue or cell (e.g., neural cell). The transport moieties can be covalently linked to the therapeutic polypeptides. The covalent link can include a peptide bond or a labile bond (e.g., a bond readily cleavable or subject to chemical change in the interior target cell environment). Additionally, the transport moieties can be cross-linked (e.g., chemically cross-linked, UV cross-linked) to the therapeutic polypeptide. The transport moieties can also be linked to the therapeutic polypeptide with linking polypeptide described herein.

The transport moieties can be repeated more than once in the therapeutic agent. The repetition of a transport moiety may affect (e.g., increase) the uptake of the peptides and/or proteins by a desired cell. The transport moiety may also be located either at the amino-terminal region of therapeutic peptide or at its carboxy-terminal region or at both regions.

In one embodiment, the transport moiety can include at least one transport peptide sequence that allows the therapeutic polypeptide once linked to the transport moiety to penetrate into the cell by a receptor-independent mechanism. In one example, the transport peptide is a synthetic peptide that contains a Tat-mediated protein delivery sequence and SEQ ID NO: 3.

Other examples of known transport moieties, subdomains and the like are described in, for example, Canadian patent document No. 2,301,157 (conjugates containing homeodomain of antennapedia) as well as in U.S. Pat. Nos. 5,652, 122, 5,670,617, 5,674,980, 5,747,641, and 5,804,604, all of which are incorporated herein by reference in their entirety, (conjugates containing amino acids of Tat HIV protein; herpes simplex virus-1 DNA binding protein VP22, a Histidine tag ranging in length from 4 to 30 histidine repeats, or a variation derivative or homologue thereof capable of facilitating uptake of the active cargo moiety by a receptor independent process.

A 16 amino acid region of the third alpha-helix of antennapedia homeodomain has also been shown to enable proteins (made as fusion proteins) to cross cellular membranes (PCT international publication number WO 99/11809 and Canadian application No.: 2,301,157. Similarly, HIV Tat protein was shown to be able to cross cellular membranes.

In addition, the transport moiety(ies) can include polypeptides having a basic amino acid rich region covalently linked to an active agent moiety (e.g., intracellular domain-containing fragments inhibitor peptide). As used herein, the term "basic amino acid rich region" relates to a region of a protein with a high content of the basic amino acids such as arginine, histidine, asparagine, glutamine, lysine. A "basic amino acid rich region" may have, for example 15% or more of basic amino acid. In some instance, a "basic amino acid rich region" may have less than 15% of basic amino acids and still function as a transport agent region. In other instances, a basic amino acid region will have 30% or more of basic amino acids.

The transport moiety(ies) may further include a proline rich region. As used herein, the term proline rich region refers to a region of a polypeptide with 5% or more (up to 100%) of proline in its sequence. In some instance, a proline rich region may have between 5% and 15% of prolines. Additionally, a proline rich region refers to a region, of a polypeptide containing more prolines than what is generally observed in naturally occurring proteins (e.g., proteins encoded by the human genome). Proline rich regions of this application can function as a transport agent region.

In one embodiment, the therapeutic peptide described herein can be non-covalently linked to a transduction agent. An example of a non-covalently linked polypeptide transduction agent is the Chariot protein delivery system (See U.S. Pat. No. 6,841,535; *J Biol Chem* 274(35):24941-24946; and *Nature Biotec.* 19:1173-1176, all herein incorporated by reference in their entirety).

In other embodiments, the therapeutic peptides can be expressed in cells being treated using gene therapy to inhibit VCP interaction or binding with the polyQ protein, such as mtHtt. The gene therapy can use a vector including a nucleotide encoding the therapeutic peptides. A "vector" (sometimes referred to as gene delivery or gene transfer "vehicle") refers to a macromolecule or complex of molecules comprising a polynucleotide to be delivered to the cell. The polynucleotide to be delivered may comprise a coding sequence of interest in gene therapy. Vectors include, for example, viral vectors (such as adenoviruses (Ad), adeno-associated viruses (AAV), and retroviruses), liposomes and other lipid-containing complexes, and other macromolecular complexes capable of mediating delivery of a polynucleotide to a target cell.

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities.

Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., Lupton, S., WO 92/08796, published May 29, 1992; and Lupton, S., WO 94/28143, published Dec. 8, 1994). Such marker genes can provide an added measure of control that can be advantageous in gene therapy contexts. A large variety of such vectors are known in the art and are generally available.

Vectors for use herein include viral vectors, lipid based vectors and other non-viral vectors that are capable of delivering a nucleotide encoding the therapeutic peptides described herein to the target cells. The vector can be a targeted vector, especially a targeted vector that preferentially binds to neurons and. Viral vectors for use in the application can include those that exhibit low toxicity to a target cell and induce production of therapeutically useful quantities of the therapeutic peptide in a cell specific manner.

Examples of viral vectors are those derived from adenovirus (Ad) or adeno-associated virus (AAV). Both human and non-human viral vectors can be used and the recombinant viral vector can be replication-defective in humans. Where the vector is an adenovirus, the vector can comprise a polynucleotide having a promoter operably linked to a gene encoding the therapeutic peptides and is replication-defective in humans.

Other viral vectors that can be used herein include herpes simplex virus (HSV)-based vectors. HSV vectors deleted of one or more immediate early genes (IE) are advantageous because they are generally non-cytotoxic, persist in a state similar to latency in the target cell, and afford efficient target cell transduction. Recombinant HSV vectors can incorporate approximately 30 kb of heterologous nucleic acid.

Retroviruses, such as C-type retroviruses and lentiviruses, might also be used in the application. For example, retroviral vectors may be based on murine leukemia virus (MLV). See, e.g., Hu and Pathak, Pharmacol. Rev. 52:493-511, 2000 and Fong et al., Crit. Rev. Ther. Drug Carrier Syst. 17:1-60, 2000. MLV-based vectors may contain up to 8 kb of heterologous (therapeutic) DNA in place of the viral genes. The heterologous DNA may include a tissue-specific promoter and a nucleic acid encoding the therapeutic peptide. In methods of delivery to neural cells, it may also encode a ligand to a tissue specific receptor.

Additional retroviral vectors that might be used are replication-defective lentivirus-based vectors, including human immunodeficiency (HIV)-based vectors. See, e.g., Vigna and Naldini, J. Gene Med. 5:308-316, 2000 and Miyoshi et al., J. Virol. 72:8150-8157, 1998. Lentiviral vectors are advantageous in that they are capable of infecting both actively dividing and non-dividing cells.

Lentiviral vectors for use in the application may be derived from human and non-human (including SIV) lentiviruses. Examples of lentiviral vectors include nucleic acid sequences required for vector propagation as well as a tissue-specific promoter operably linked to a therapeutic peptide encoding nucleic acid. These former may include the viral LTRs, a primer binding site, a polypurine tract, att sites, and an encapsidation site.

In some aspects, a lentiviral vector can be employed. Lentiviruses have proven capable of transducing different types of CNS neurons (Azzouz et al., (2002) *J Neurosci.* 22: 10302-12) and may be used in some embodiments because of their large cloning capacity.

A lentiviral vector may be packaged into any lentiviral capsid. The substitution of one particle protein with another from a different virus is referred to as "pseudotyping". The vector capsid may contain viral envelope proteins from other viruses, including murine leukemia virus (MLV) or vesicular stomatitis virus (VSV). The use of the VSV G-protein yields a high vector titer and results in greater stability of the vector virus particles.

Alphavirus-based vectors, such as those made from semliki forest virus (SFV) and sindbis virus (SIN) might also be used in the application. Use of alphaviruses is described in Lundstrom, K., Intervirology 43:247-257, 2000 and Perri et al., Journal of Virology 74:9802-9807, 2000.

Recombinant, replication-defective alphavirus vectors are advantageous because they are capable of high-level heterologous (therapeutic) gene expression, and can infect a wide target cell range. Alphavirus replicons may be targeted to specific cell types by displaying on their virion surface a functional heterologous ligand or binding domain that would allow selective binding to target cells expressing a cognate binding partner. Alphavirus replicons may establish latency, and therefore long-term heterologous nucleic acid expression in a target cell. The replicons may also exhibit transient heterologous nucleic acid expression in the target cell.

In many of the viral vectors compatible with methods of the application, more than one promoter can be included in the vector to allow more than one heterologous gene to be expressed by the vector. Further, the vector can comprise a sequence, which encodes a signal peptide or other moiety, which facilitates expression of the therapeutic peptide from the target cell.

To combine advantageous properties of two viral vector systems, hybrid viral vectors may be used to deliver a nucleic acid encoding a therapeutic peptide to a target neuron, cell, or tissue. Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and adenoviral ITRs may be used to transduce cells. In another variation, an AAV vector may be placed into a "gutless", "helper-dependent" or "high-capacity" adenoviral vector. Adenovirus/AAV hybrid vectors are discussed in Lieber et al., J. Virol. 73:9314-9324, 1999. Retrovirus/adenovirus hybrid vectors are discussed in Zheng et al., Nature Biotechnol. 18:176-186, 2000. Retroviral genomes contained within an adenovirus may integrate within the target cell genome and effect stable gene expression.

Other nucleotide sequence elements, which facilitate expression of the therapeutic peptide and cloning of the vector are further contemplated. For example, the presence of enhancers upstream of the promoter or terminators downstream of the coding region, for example, can facilitate expression.

In accordance with another embodiment, a tissue-specific promoter can be fused to nucleotides encoding the therapeutic peptides described herein. By fusing such tissue specific promoter within the adenoviral construct, transgene expression is limited to a particular tissue. The efficacy of gene expression and degree of specificity provided by tissue specific promoters can be determined, using the recombinant adenoviral system of the present application. Neuron specific promoters, such as the platelet-derived growth factor β-chain (PDGF-β) promoter and vectors, are well known in the art.

In addition to viral vector-based methods, non-viral methods may also be used to introduce a nucleic acid encoding a therapeutic peptide into a target cell. A review of non-viral methods of gene delivery is provided in Nishikawa and Huang, Human Gene Ther. 12:861-870, 2001. An example of a non-viral gene delivery method according to the application employs plasmid DNA to introduce a nucleic acid encoding a therapeutic peptide into a cell. Plasmid-based gene delivery methods are generally known in the art.

Synthetic gene transfer molecules can be designed to form multimolecular aggregates with plasmid DNA. These aggregates can be designed to bind to a target cell. Cationic amphiphiles, including lipopolyamines and cationic lipids, may be used to provide receptor-independent nucleic acid transfer into target cells.

In addition, preformed cationic liposomes or cationic lipids may be mixed with plasmid DNA to generate cell-transfecting complexes. Methods involving cationic lipid formulations are reviewed in Feigner et al., Ann. N.Y. Acad. Sci. 772:126-139, 1995 and Lasic and Templeton, Adv. Drug Delivery Rev. 20:221-266, 1996. For gene delivery, DNA may also be coupled to an amphipathic cationic peptide (Fominaya et al., J. Gene Med. 2:455-464, 2000).

Methods that involve both viral and non-viral based components may be used according to the application. For example, an Epstein Barr virus (EBV)-based plasmid for therapeutic gene delivery is described in Cui et al., Gene Therapy 8:1508-1513, 2001. Additionally, a method involving a DNA/ligand/polycationic adjunct coupled to an adenovirus is described in Curiel, D. T., Nat. Immun 13:141-164, 1994.

Additionally, the nucleic acid encoding the therapeutic peptides can be introduced into the target cell by transfecting the target cells using electroporation techniques. Electroporation techniques are well known and can be used to facilitate transfection of cells using plasmid DNA.

Vectors that encode the expression of the therapeutic peptides can be delivered in vivo to the target cell in the form of an injectable preparation containing pharmaceutically acceptable carrier, such as saline, as necessary. Other pharmaceutical carriers, formulations and dosages can also be used in accordance with the present application.

Where the target cell includes a nerve cell being treated, the vector can be delivered at an amount sufficient for the therapeutic peptide to be expressed to a degree, which allows for highly effective therapy. The therapeutic peptide can be expressed for any suitable length of time within the target cell, including transient expression and stable, long-term expression. In one aspect of the application, the nucleic acid encoding the therapeutic peptide will be expressed in therapeutic amounts for a defined length of time effective to inhibit neurodegeneration in the subject being treated. In another aspect, the nucleic acid encoding the therapeutic peptide will be expressed in therapeutic amounts for a defined length of time effective to increase survival rate of neurons.

The therapeutic agents described herein may be modified (e.g., chemically modified). Such modification may be designed to facilitate manipulation or purification of the molecule, to increase solubility of the molecule, to facilitate administration, targeting to the desired location, to increase or decrease half life. A number of such modifications are known in the art and can be applied by the skilled practitioner.

In the methods of treatment disclosed herein, a therapeutically effective amount of the therapeutic agent is administered to the subject to treat a polyQ protein associated neurodegenerative disease. In one embodiment, a formulation including the therapeutic agent can be administered to the subject systemically in the period from the time of, for example, up to hours, days, and/or weeks after the disease or disorder is diagnosed.

The therapeutic agents can be delivered to a subject by any suitable route, including, for example, local and/or systemic administration. Systemic administration can include, for example, parenteral administration, such as intramuscular, intravenous, intraarticular, intraarterial, intrathecal, subcutaneous, or intraperitoneal administration. The agent can also be administered orally, transdermally, topically, by inhalation (e.g., intrabronchial, intranasal, oral inhalation or intranasal drops) or rectally. In some embodiments, the therapeutic agent can be administered to the subject via intravenous administration using an infusion pump to deliver daily, weekly, or doses of the therapeutic agent.

Pharmaceutically acceptable formulations of the therapeutic agent can be suspended in aqueous vehicles and introduced through conventional hypodermic needles or using infusion pumps.

For injection, therapeutic agent can be formulated in liquid solutions, typically in physiologically compatible buffers such as Hank's solution or Ringer's solution. In addition, the therapeutic agent may be formulated in solid form and re-dissolved or suspended immediately prior to use. Lyophilized forms are also included. The injection can be, for example, in the form of a bolus injection or continuous infusion (such as using infusion pumps) of the therapeutic agent.

It will be appreciated that the amount, volume, concentration, and/or dosage of the therapeutic agent that is administered to any one animal or human depends on many factors, including the subject's size, body surface area, age, the particular composition to be administered, sex, time and route of administration, general health, and other drugs being administered concurrently. Specific variations of the above noted amounts, volumes, concentrations, and/or dosages of therapeutic agent can be readily be determined by one skilled in the art using the experimental methods described below.

In some embodiments, a therapeutic agent, such as a therapeutic peptide described herein, can be administered can be administered locally and/or systemically to a subject in need thereof at a dose or amount of about 0.1 μmol, about 1 μmol, about 5 μmol, about 10 μmol, or more; or about 0.0001 mg/kg, about 0.001 mg/kg, about 0.01 mg/kg, about 0.1 mg/kg, or about 1 mg/kg to about 5 mg/kg or 10 mg/kg of the subject being treated. The therapeutic agent can be administered daily, weekly, biweekly, monthly or less frequently.

In some embodiments, the therapeutic agent can be administered to the subject at an amount effective to increase plasma levels of NAD+, FAD, and/or citrate in the subject. As shown in the Examples, treatment with HV-3 in R6/2 mice significantly increased the plasma content of $NAD^+$, FAD, and citrate (Table 1). NAD and FAD are central biomolecules involved in energy production and mitochondrial metabolic activity; declines in NAD and FAD levels reflect decreased mitochondrial number, density, and activity. Thus, the findings here in parallel demonstrated that mtHtt-induced mitochondria-accumulated VCP causes mitochondrial dysfunction and global energy deficits in HD, leading to neuronal cell death. Because the depletion in NAD was noted in HD patient cells and blood, normalization of NAD content in HD mouse plasma by HV-3 treatment can provide a biomarker amenable for therapeutic intervention.

In another embodiment, the therapeutic agent can be administered to a subject systemically by intravenous injection or locally at the site of injury, usually within about 24 hours, about 48 hours, about 100 hours, or about 200 hours or more of when an injury occurs (e.g., within about 6 hours, about 12 hours, or 24 hours, inclusive, of the time of the injury).

In other embodiments, a pharmaceutically acceptable formulation used to administer the therapeutic agent(s) can also be formulated to provide sustained delivery of the active compound to a subject. For example, the formulation may deliver the active compound for at least one, two, three, or four weeks, inclusive, following initial administration to the subject. For example, a subject to be treated in accordance with the method described herein can be treated with the therapeutic agent for at least 30 days (either by repeated administration or by use of a sustained delivery system, or both).

Approaches for sustained delivery include use of a polymeric capsule, a minipump to deliver the formulation, a biodegradable implant, or implanted transgenic autologous cells (see U.S. Pat. No. 6,214,622) Implantable infusion pump systems (e.g., INFUSAID pumps (Towanda, Pa.)); see Zierski et al., 1988; Kanoff, 1994) and osmotic pumps (sold by Alza Corporation) are available commercially and otherwise known in the art. Another mode of administration is via an implantable, externally programmable infusion pump. Infusion pump systems and reservoir systems are also described in, e.g., U.S. Pat. No. 5,368,562 and No. 4,731,058.

Vectors encoding the therapeutic peptides can often be administered less frequently than other types of therapeutics. For example, an effective amount of such a vector can range from about 0.01 mg/kg to about 5 or 10 mg/kg, inclusive; administered daily, weekly, biweekly, monthly or less frequently.

The following examples are included to demonstrate different embodiments of the invention. It should be appreciated by those of skill in the art that the techniques disclosed in the examples, which follow represent techniques discovered by the inventor to function well in the practice of the claimed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the claims.

Example 1

In this Example we show that VCP was aberrantly translocated to the mitochondria where it was bound to mtHtt in a variety of HD models in vitro and in vivo. Such accumulation of VCP on mitochondria resulted in excessive mitophagy, mitochondrial mass loss, and subsequent neuronal degeneration in HD models in culture and in animals. Significantly, blocking VCP translocation to mitochondria by a novel peptide HV-3 that interferes with VCP and mtHtt interaction inhibited VCP-mediated mitophagy impairment, suppressed mitochondrial dysfunction, and reduced HD-associated neuropathology and motor deficits in two HD transgenic mouse models.

Materials and Methods

Antibodies and Reagents

Protein phosphatase inhibitor and protease inhibitor cocktails were purchased from Sigma-Aldrich. VCP inhibitor Eer I and proteasome inhibitor MG132 were from Tocris Bioscience. Antibodies for Tom20 (sc-11415, 1:1000), c-Myc (sc-40, 1:1000), GFP (sc-9996, 1:1000), GST (sc-138, 1:500) and Parkin (sc-32282, 1:1000) were from Santa Cruz Biotechnology. Full-length Htt (MAB2166, 1:1000), polyQ (MAB1574, 1:1000), EM48 (MAB5374, 1:1000) and NeuN (MAB377, 1:500) antibodies were from Millipore. Pan-actin (A1978, 1:10,000) and Flag (F3165, 1:5000) antibodies were from Sigma-Aldrich. Antibodies for VDAC (ab14734, 1:2000) and VCP (ab109240, 1:10000) were from Abcam. EEA1 (3288, 1:500) and LC3 (2775, 1:1000) antibodies were from Cell Signaling, WFS1 (NB100-1918, 1:1000) antibody was from Novus, HMGB1 (high-mobility group box B1, 10829-1-AP, 1:1000) antibody was from Proteintech, and GRP78 (ADI-SPA-826, 1:1000) and Calnexin (ADI-SPA-860, 1:1000) antibody was from Enzo Life Sciences. Anti-mouse IgG and anti-rabbit IgG, peroxidase-linked, species-specific antibodies were from Thermo-Scientific. The Htt/VCP peptides were synthesized by American Peptide Company, Inc., and conjugated to TAT-carrier peptide (amino acids 47-57) for transmembrane delivery. Note that $TAT_{47-57}$-based delivery was used in culture and in vivo and was found to be safe and efficacious for delivery of peptide cargoes to cells and also to cross the blood-brain barrier.

Constructs and Transfection

Myc-tagged full-length Htt with 23Q or 73Q plasmid was obtained from the CHDI foundation. The full-length VCP wild-type ($VCP^{WT}$) and GFP-LC3B plasmids were obtained from Addgene. To construct the mitochondria-targeting VCP plasmid, CMV-mito-GEM-GECO1 was digested with BamHI and Hind III, and VCP was PCR-amplified and inserted into the plasmid backbone. Site mutation of the VCP plasmid was performed using a site-mutagenesis kit (Agilent Technologies, Inc.). Cells were transfected with TransITC®-2020 (Mirus Bio LLC) following the manufacturer's protocol.

Cell Culture

Immortalized striatal cell lines HdhQ111 mutant and HdhQ7 wild-type derived from striatal cells from HdhQ111/

111 and HdhQ7/Q7 knock-in transgenic mice (expressing 111 and 7 glutamine repeats, respectively) were obtained from the CHDI Foundation. Cells were cultured in DMEM supplemented with 10% FBS, 100 µg/ml penicillin, 100 µg/ml streptomycin, and 400 µg/ml G418. Cells were grown at 33° C. in a 5% $CO_2$ incubator. Cells within 14 passages were used in all experiments.

Human cervix carcinoma cells (HeLa cells) and HEK293 cells were maintained in DMEM supplemented with 10% FBS and 1% (v/v) penicillin/streptomycin.

Primary striatal neurons from E18 rat midbrain tissue (BrainBits, Springfield, Ill., USA) were seeded on cover slides that were coated with poly-D-lysine/laminine and grown in neurobasal medium supplemented with 2% B27 and 0.5 mM glutamate. At 7 DIV, cells were transfected with the control vector or flag-VCP$^{mt}$ using TransIT®-2020 Transfection Reagent combined with formulated BrainBits transfection media for primary neurons (BrainBits, USA).

iPS cells from normal subjects and HD patients were differentiated into neurons using the protocol from our previous studies. Neurons (about 5,000 cells) were plated onto 12-mm poly-D-lysine/laminine-coated coverslips and grown in 24-well plates in neuronal differentiation medium as described previously.

All of the above cells were maintained at 37° C. in 5% $CO_2$-95% air.

RNA Interference

For silencing Htt and VCP in HD striatal cells, control siRNA, mouse Htt and mouse VCP siRNA were purchased from Thermo Fisher Scientific. HdhQ7 and HdhQ111 cells were transfected either with control siRNA, or Htt or VCP siRNA using TransIT-TKO® Transfection Reagent (Mirus Bio LLC), according to the manufacturer's instructions.

Isolation of Mitochondria-Enriched, ER-Enriched and Cytosolic Fractions

Cells were washed with cold PBS and incubated on ice for 30 minutes in a lysis buffer (250 mM sucrose, 20 mM HEPES-NaOH, pH 7.5, 10 mM KCl, 1.5 mM $MgCl_2$, 1 mM EDTA, protease inhibitor cocktail and phosphatase inhibitor cocktail). Mice brains were minced and homogenized in lysis buffer and then placed on ice for 30 minutes. Collected cells or tissue were disrupted 20 times by repeated aspiration through a 25-gauge needle, followed by a 30-gauge needle. The homogenates were spun at 800 g for 10 minutes at 4° C., and the resulting supernatants were spun at 10,000 g for 20 minutes at 4° C. The pellets were washed with lysis buffer and spun at 10,000 g again for 20 minutes at 4° C. The final pellets were suspended in lysis buffer containing 1% Triton X-100 and were mitochondrial-rich lysate fractions. The supernatant was centrifuged at 100,000 g, 4° C., for 1 hour, the pellets were suspended in lysis buffer containing 1% Triton X-100 as ER fractions. The final supernatant was cytosolic fractions. The mitochondrial proteins VDAC and the ER protein WFS1 were used as loading controls for mitochondria and ER fractions, respectively.

Immunoprecipitation

Cells were lysed in a total cell lysate buffer (50 mM Tris-HCl, pH 7.5, containing 150 mM NaCl, 1% Triton X-100, and protease inhibitor) or in a mitochondrial isolation buffer (250 mM sucrose, 20 mM HEPES-NaOH, pH 7.5, 10 mM KCl, 1.5 mM $MgCl_2$, 1 mM EDTA, protease inhibitor cocktail, and phosphatase inhibitor cocktail). Total lysates or mitochondrial lysates or the mixture of ER and cytosolic fractions were incubated with the indicated antibodies overnight at 4° C. followed by the addition of protein A/G beads for 1 hour Immunoprecipitates were washed four times with cell lysate buffer and were analyzed by SDS-PAGE and immunoblotting.

Rational Design of Peptide Inhibitor

Two nonrelated proteins that interact in an inducible manner have often shared short sequences of homology that represent sites of both inter- and intra-molecular interactions. Similar to the peptide design for PKC peptide deltaV1-1 and Drp1 peptide P110, we used L-ALIGN sequence alignment software and identified two different regions of homology between VCP (VCP, Human, AAI21795) and Htt (Htt, human, NP_002102). These regions are marked as regions HV from 1 to 4. We found that all the homologous sequences are conserved in a variety of species including human, mouse, rat and fish. We synthesized the four peptides commercially corresponding to regions HV1-4 and conjugated them to the cell permeating TAT protein-derived peptide, $TAT_{47-57}$, as we described. These peptides are referred to as HV-1, HV-2, HV-3 and HV-4. The purity was assessed as >98% by mass spectrometry. Lyophilized peptides were dissolved in sterile water and stored at −80° C. until use.

Measurement of Cell Viability

HdhQ7 and Q111 mouse striatal cells were treated with the HV-3 peptide or the control peptide TAT (3 µM, each) in an FBS-free DMEM medium or in DMEM containing 10% serum for 24 hours. Medium from the cultured cells was harvested. Proteins from the medium were purified using Amicon Ultra 0.5 ml centrifugal filters (Millipore). HMGB1 release into the medium was then analyzed by Western blotting with anti-HMGB1 antibody. In parallel, cell death was determined by measuring LDH release into the culture medium, as described previously.

Immunocytochemistry

Cells cultured on coverslips were washed with cold PBS and fixed in 4% formaldehyde, and then permeabilized with 0.1% Triton X-100. After incubation with 2% normal goat serum (to block nonspecific staining), fixed cells were incubated overnight at 4° C. with indicated primary antibodies. Cells were washed with PBS and incubated for 60 minutes with Alexa Fluor 568, 488 or 405 secondary antibody, followed by incubation with Hoechst dye (1:10,000; Invitrogen) for 10 minutes. Coverslips were mounted, and slides were imaged by confocal microscopy (Fluoview FV100; Olympus).

To determine mitochondrial mass in cultures, cells were stained with antibodies against Tom20 or stained with Mitotracker green. The fluorescent density of Tom20 (1:500) or mitotracker green was quantitated using NIH Image J software. To measure the membrane potential of mitochondria in cultures, cells were incubated with 0.25 µM tetramethyl rhodamine (TMRM) (Invitrogen Life Science) for 20 minutes at 37° C. To determine lysosomal activity, cells were incubated with Lyso-ID Red dye (Enzo Life Science) for 30 min at 37° C. The images were visualized by microscope and quantitation of the density of red fluorescence was carried out using NIH ImageJ software as described previously. For immunocytochemistry study, at least 100 cells/group were counted and quantitated by an observer blind to experimental conditions.

In patient-iPS cell-derived neurons, to ensure the observation of mitochondria in the medium spiny neurons, the cells were stained with a mitochondrial marker (anti-TOM20, 1:500) and markers for medium spiny neurons (DARPP-32, 1:200, Epitomics), as we previously described. At least 50 neurons/group were counted and quantitated.

Animal Model of HD

All experiments in animals were conducted in accordance with protocols approved by the Institutional Animal Care and Use Committee of Case Western Reserve University and were performed based on the National Institutes of Health Guide for the Care and Use of Laboratory Animals. Sufficient procedures were employed for reducing pain or discomfort of subjects during the experiments.

Male R6/2 mice and their wild-type (WT) littermates were purchased from Jackson Laboratories [Bar Harbor, Me.; B6CBA-TgN (HD exon1)62; JAX stock number: 006494]. These mice are transgenic for the 5' end of the human HD gene carrying 100-150 glutamine (CAG) repeats.

YAC128 [FVB-Tg(YAC128)53Hay/J, JAX stock number: 004938] breeders were purchased from Jackson Laboratories. The YAC128 mice contain a full-length human huntingtin gene modified with a 128 CAG repeat expansion in exon 1. The mice were mated, bred, and genotyped in the animal facility of Case Western Reserve University. Male mice were used in the study.

All of the mice were maintained with a 12-hour light/dark cycle (on 6 am, off 6 pm).

Systemic Peptide Treatment in HD Mice

All randomization and peptide treatments were prepared by an experimenter not associated with behavioral and neuropathology analysis.

Male hemizygous R6/2 mice (Tg) and their age-matched wild-type littermates (Wt) were implanted with a 28-day osmotic pump (Alzet, Cupertino Calif.) containing TAT control peptide or HV-3 peptide, which delivered peptides to the mice at a rate of 3 mg/kg/day. The first pump was implanted subcutaneously in the back of 5-week-old mice between the shoulders and replaced once, after 4 weeks.

YAC128 mice (Tg) and their age-matched wild-type littermates (WT) were implanted with an osmotic pump containing TAT control peptide or HV-3 peptide (3 mg/kg/day, each) starting from the age of 3 months. The pump was replaced once every month. By the age of 12 months, the treatments were terminated and the mouse samples were harvested for analysis.

Behavioral Analysis in HD Mice

All behavioral analyses were conducted by an experimenter who was blind to genotypes and treatment groups.

Activity Chamber

Gross locomotor activity was assessed in R6/2 mice and age-matched wild-type littermates at the ages of 13 weeks and in YAC128 mice and age-matched wild-type littermates at the ages of 2, 3, 6, 9, and 12 months. In an activity chamber (Omnitech Electronics, Inc), mice were placed in the center of the chamber and allowed to explore while being tracked by an automated beam system (Vertax, Omnitech Electronics Inc). Distance moved, horizontal, vertical, and rearing activities were recorded. Because R6/2 mice were sensitive to changes in environment and handling, we only conducted one-hour locomotor activity analysis for R6/2 mice and wild-type littermates. We performed 24 hours of locomotor activity analysis for YAC128 mice and their wild-type littermates.

Clasping Behavior

Hindlimb clasping was assessed with the tail suspension test once a week from the ages 8 to 11 weeks in R6/2 mice. Mice were suspended by the tail for 60 seconds and the latency for the hindlimbs or all four paws to clasp was recorded using the score system: Clasping over 10 seconds, score 3; 5-10 seconds, score 2; 0-5 seconds, score 1; 0 seconds, score 0.

Rotarod Analysis

The motor coordination and balance of YAC128 mice were tested on an accelerating Rotarod (IITC Life Sciences, Serials 8) at the ages of 2, 3, 6, 9 and 12 months. Training and baseline testing for motor function tasks were conducted at 2 months of age. For training, mice were given three 120-second trials per day at a fixed-speed of 15 rpm for three consecutive days. During the testing phase, the Rotarod accelerated from 5 to 40 rpm over 3 minutes; the maximum score was 300 seconds. Rotarod scores were the average of three trials per day (with 2 hours rest between trials) for 3 consecutive days.

The body weight and survival rate of HD mice and wild-type littermates were recorded throughout the study period.

Immunohistochemistry and Stereological Measurements

Mice were deeply anesthetized and transcardially perfused with 4% paraformaldehyde in 0.1 M phosphate buffer (PB; pH 7.4). Brains were processed for paraffin embedment. Brain sections (5 µm, coronal) were used for immunohistochemical localization of DARPP-32 (1:500, Epitomics) using the IHC Select HRP/DAB kit (Millipore). Quantitation of DARPP-32 immunostaining was described in our previous study. The same image exposure times and threshold settings were used for sections from all treatment groups.

To measure the number of NeuN-positive cells, a series of 25 mm thick coronal sections spaced 200 mm apart spanning the striatum were stained with NeuN antibody (Millipore, 1:500) and visualized by diaminobenzidine. For neuropathological analyses, brain sections were analyzed stereologically as described previously. Briefly, unbiased stereological counts of NeuN-positive neurons within the striatum were performed using unbiased stereological principles and analyzed with StereoInvestigator software (Microbrightfield, Williston, Vt.). Optical fractionator sampling was carried out on a Leica DM5000B microscope (Leica Microsystems, Bannockburn, Ill.) equipped with a motorized stage and Lucivid attachment (40× objective). The following parameters were used in the final study: grid size, (X) 500 (Y) 500 µm; Counting frame, (X) 68.2 µm, (Y) 75 µm, depth was 20 µm. Gundersen coefficients of error for m=1 were all less than 0.10. Stereologic estimations were performed with the same parameters in striatum of wt or YAC transgenic mice treated with the control peptide or peptide HV-3 (n=6 mice/group). The total volume of stratial tissue measured in each brain is calculated by StereoInvestigator and the neuronal density is presented as Neu-N positive cell number per mm$^3$.

Quantitation was conducted by an experimenter blind to the experimental groups.

Electron Microscopy

Small pieces of the striata tissue were fixed by immersion in triple aldehyde-DMSO. After rinsing in 0.1 M phosphate buffer (pH 7.3), the tissues were post-fixed in ferrocyanide-reduced osmium tetroxide. Water rinse was followed by overnight soaking in acidified uranyl acetate. After rinsing in distilled water, the tissue blocks were dehydrated in ascending concentrations of ethanol, passed through propylene oxide, and embedded in Poly/Bed resin. Thin sections were sequentially stained with acidified uranyl acetate followed by a modification of Sato's triple lead stain. These sections were examined in a FEI Tecnai Spirit (T12) transmission electron microscope with a Gatan US4000 4 k×4 k CCD at the Case Western Reserve University EM core facility. Mitochondria from 15 random areas in each animal were imaged by an experimenter blind to the experimental groups. The number of mitophagosomes per 100 um$^2$ was counted.

Western Blot Analysis

Protein concentrations were determined by Bradford assay. Protein was then resuspended in Laemmli buffer, loaded on SDS-PAGE, and transferred onto nitrocellulose membranes. Membranes were probed with the indicated antibody, followed by visualization with ECL.

Statistical Analysis

Sample sizes are determined by power analysis based on pilot data collected by our labs or published studies. In animal studies, we used n=15-18 mice/group for behavioral tests, n=6 mice/group for biochemical analysis and n=6 mice/group for pathology studies. In cell culture studies, we performed each study with three independent replications. For all of the animal studies, we have ensured randomization and blinded conduct of experiments. For all imaging analysis, the quantitation was conducted by an observer who was blind to the experimental groups.

Data were analyzed by Student's t test or one-way ANOVA with post-hoc Tukey test or One-way ANOVA with Scheffe post hoc test for comparison between two groups. Survival and body weight were analyzed by repeated-measures two-way ANOVA. Data are expressed as mean±SEM. Statistical significance was considered achieved when the value of p was <0.05.

Results

VCP was Recruited to Mitochondria by mtHtt in HD

Figure 1:
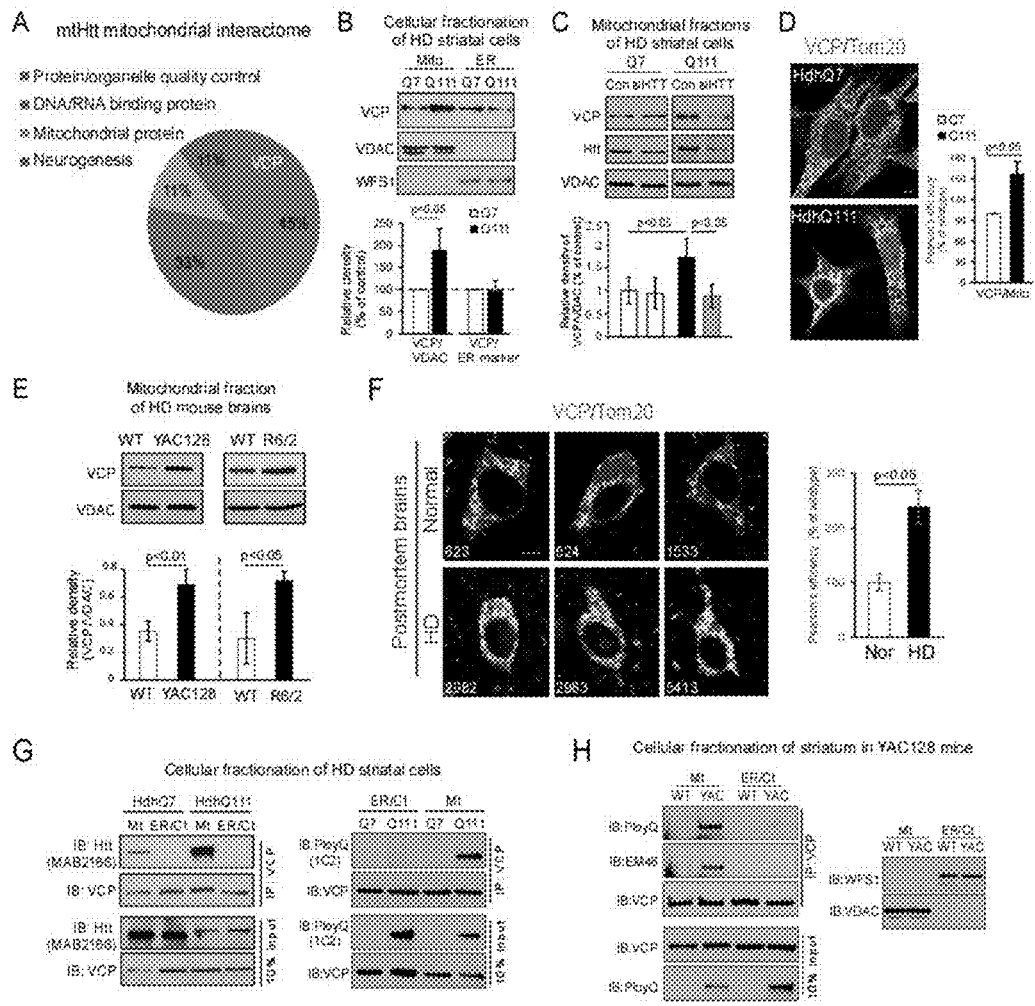
FIGS. 1(A-H) illustrate: VCP was recruited to mitochondria by mtHtt and bound to mitochondria-associated mtHtt in vitro and in vivo. (A) Affinity purification followed by tandem mass spectrometry analysis was conducted to identify mtHtt-binding proteins on mitochondria in HD knock-in mouse HdhQ7 and HdhQ111 striatal cells. Shown is the molecular and cellular function of the mtHtt mitochondrial interactome in HdhQ111 cells. Among these proteins, VCP was the leading candidate for an mtHtt-binding protein.

We used HD mouse striatal HdhQ111 (mutant) and HdhQ7 (wild-type) cells to profile the interactome of mtHtt on mitochondria (FIG. 1A). HdhQ111 and Q7 cells were immortalized from knock-in mice carrying 111 and 7 CAG, respectively, in the mouse htt gene. These cell lines have been widely used as a cell culture model to study HD. We isolated mitochondria from these cultured striatal cells, and conducted immunoprecipitation (IP) of mitochondrial fractions with anti-MAB2166 antibody that recognizes both wild-type (wt) and mutant (mt) Htt. Tandem mass spectrometry analysis following affinity purification identified 9 proteins that putatively bound to mitochondria-associated mtHtt in HdhQ111 but not wt Htt in HdhQ7 striatal cells (FIG. 1A). Among these proteins, VCP was the leading candidate that bound to mtHtt on mitochondria of HdhQ111 cells (FIG. 1A).

Before validating this proteomic analysis on the interaction between VCP and mtHtt, we first want to confirm whether VCP is localized on mitochondria in models of HD. Western blot analysis of cellular fractionations revealed that VCP was markedly enriched in the mitochondria of HdhQ111 cells relative to those in HdhQ7 cells (FIG. 1B), while there was no increase in the recruitment of VCP to the ER in HdhQ111 cells when compared to that of HdhQ7 cells (FIG. 1B). Reduction of mtHtt levels by treatment of HdhQ111 cells with Htt small interfering RNA (siRNA) abolished VCP translocation to the mitochondria (FIG. 1C), indicating that mtHtt is required for VCP recruitment to the mitochondria. Confocal imaging analysis consistently showed increased localization of VCP on mitochondria, but not on the ER and endosome of HdhQ111 striatal cells, relative to that in HdhQ7 cells (FIG. 1D). A similar enrichment of VCP on mitochondria was further observed in mitochondrial fractions isolated from the striatum of both R6/2 mice at the age of 9 weeks and YAC128 mice at the age of 6 months (FIG. 1E). To test whether VCP accumulation on mitochondria also exists in human HD, we analyzed VCP localization on mitochondria by confocal microscopy in the caudate nucleus of postmortem brains from three HD patients and three normal subjects. We observed greater localization of VCP on mitochondria in HD patient brains than in normal subjects (FIG. 1F). These data collectively demonstrate that VCP is recruited to and accumulated on mitochondria in HD. Because there was no evidence of increased VCP to mitochondria in response to Parkinson's disease-associated mutants, VCP recruitment to mitochondria is likely to be disease- or stress-dependent.

Next, we isolated mitochondria, ER, and cytosolic fractions from HdhQ7 and HdhQ111 mouse striatal cells, and conducted IP with anti-VCP antibody followed by immunoblotting (IB) with anti-MAB2166 antibody. We observed mtHtt proteins in VCP immunoprecipitates of mitochondrial fractions but not in that of ER and cytosolic fractions in HdhQ111 mouse striatal cells (FIG. 1G-left panel). Although VCP interacted with wt Htt on the mitochondria in HdhQ7 striatal cells, the extent is much lesser than that in HdhQ111 cells only expressing mtHtt (FIG. 1G-left panel). To further validate the interaction between VCP and mtHtt, we performed IP analysis with anti-VCP antibody followed by IB with anti-1C2 antibody that recognizes only expanded polyQ proteins. As shown in FIG. 1G-right panel, VCP only bound to mtHtt in mitochondrial fractions, not in ER or cytosolic fractions of HdhQ111 striatal cells, even though mtHtt was expressed in the ER and cytosolic fractions. Consistently, mtHtt recognized either by anti-1C2 antibody or by anti-EM48 antibody [Note: EM48 antibody preferentially reacts with full-length human mtHtt in mice (40)] was observed in VCP immunoprecipitates of mitochondrial fractions isolated from the striata of YAC128 mice at the age of 6 months (FIG. 1H). Again, there was no obvious binding of VCP and mtHtt observed in the ER or cytosolic fractions of YAC128 mouse striata (FIG. 1H). A recent proteomic analysis of the Htt interactome in total brain lysates of BACHD transgenic mice supported our finding that VCP is a binding protein of Htt and that increased interaction between VCP and mtHtt is relevant to HD. Now we are able to locate this interaction with mitochondria in models of HD in culture and in animals.

VCP plays a central role in protein degradation by binding to its substrates. We found that treatment with either MG132, a proteasome inhibitor to prevent protein degradation, or Eeyarestatin I (Eer I), an inhibitor that blocks VCP substrate degradation, did not affect Htt or mtHtt protein levels in HdhQ or HdhQ111 cells, respectively. These data excludes the possibility that Htt or mtHtt is a substrate of VCP on mitochondria.

Together, our findings show that VCP is selectively recruited to mitochondria in models of HD where it interacts with mitochondria-bound mtHtt.

Development of a Peptide Inhibitor to Interfere with Htt/VCP Interaction

We used L-ALIGN sequence alignment software to identify two different regions of homology between VCP (human, AAI21795) and Htt (human, NP_002102) (FIG. 2A). The four regions are marked as regions HV-1 to HV-4 (FIG. 2B). We synthesized peptides corresponding to the four homologous regions between VCP and Htt (FIG. 2A), and conjugated them to the cell permeating TAT protein-derived peptide, $TAT_{47-57}$, to enable in vivo delivery, as we previously described. These peptides are referred to as HV-1, HV-2, HV-3, and HV-4. By incubating these peptides with a mixture of GST-VCP and total lysates of mouse brains (expressing full-length Htt) followed by GST pull down analysis, we found that only the addition of peptide HV-3 blocks the interaction of VCP/Htt in this in vitro binding assay (FIG. 8A). In HEK293 cells co-expressing Myc-tagged full-length Htt with 23 or 73 CAG repeats (Myc-23Q FL or Myc-73Q FL, respectively) and GFP-VCP, consistent with our observation shown in FIG. 1G and HD, VCP was preferentially bound to Myc-73Q FL (mtHtt) over Myc-23Q FL (FIG. 2C-left panel). Of four peptides, only treatment with HV-3 peptide (3 µM/day for two days) greatly blocked the VCP/mtHtt interaction in Myc-73Q FL expressing cells (FIG. 2C, FIG. 8B).

Peptide HV-3 is derived from the Htt c-terminal and corresponds to the sequence in the D1 domain of VCP (FIGS. 2A and B). The sequence of HV-3 in Htt is highly conserved among species (FIG. 8C). In addition to Htt and VCP, there is no sequence identity or similarity found between HV-3 and other proteins by the BLAST (basic local alignment search tool) analysis. Molecular docking analysis indicated that the peptide HV-3 is bound to the surface of VCP structure (FIG. 8D). Deletion of the sequence in VCP corresponding to HV-3 peptide abolished the interaction between Htt and VCP (FIG. 8E). These data suggest that HV-3 may represent an important interaction region for VCP in Htt. Therefore, we selected HV-3 as a peptide candidate that interferes with VCP/mtHtt binding.

In HdhQ7 and HdhQ111 mouse striatal cells, we treated cells with HV-3 or control peptide TAT (3 µM/day for 3 days, each) and determined VCP mitochondrial levels. Treatment with HV-3 abolished VCP translocation to mitochondria in HdhQ111 cells relative to cells treated with TAT, while HV-3 had minor effects on VCP mitochondrial levels in HdhQ7 cells (FIG. 2D). In YAC128 mice which express a full-length human mtHtt, we treated the mice with peptide HV-3 or control peptide TAT (3 mg/kg/day, each) using an osmotic mini pump starting at the age of 3 months. Consistently, the treatment abolished VCP translocation to the mitochondria of the striatum in YAC 128 mice at the age of 6 months relative to YAC128 mice treated with control peptide TAT (FIG. 2E). Note that a FITC-positive signal was observed in neurons of mouse brain after 2 days of continual systemic delivery of FITC-conjugated HV-3, supporting our idea that the peptide HV-3 can enter and accumulate in cells of brains. Unlike YAC128 mice, HD R6/2 mice express exon 1 of the human HD gene carrying more than 120 CAG repeats. Surprisingly, HV-3 treatment still blocked the VCP translocation to the mitochondria that occurred in the R6/2 mouse striatum (FIG. 2F). The toxic form of Htt (N-terminal fragment Htt) undergoes conformational rearrangement that leads to intramolecular proximity between the N domain and the polyproline region of Htt at the C-terminal. It is possible that such a conformational change results in the binding of VCP to both the full-length and the fragment of Htt. HV-3 may block the VCP accumulation on the mitochondria by disrupting the interaction between VCP and the complex of fragment/full-length Htt. Finally, we found that HV-3 treatment had no effects on VCP total protein levels in cultured HD mouse striatal cells or in the brains of R6/2 and YAC128 mice.

Suppression of VCP Association with Mitochondria by Peptide HV-3 Reduced Mitochondrial Damage and Cell Death in HD Mouse- and Patient-Derived Cells We next examined the effects of HV-3 treatment on mitochondrial function and cell survival in HD cell cultures. Mitochondrial depolarization and mitochondrial fragmentation are featured in experimental models of HD and human HD. As shown in FIGS. 3A and B, treatment with HV-3 markedly improved the mitochondrial membrane potential (MMP) and reduced the number of fragmented mitochondria in HdhQ111 striatal cells, compared to the cells treated with control peptide TAT, suggesting a reduction of mitochondrial damage. In HdhQ111 striatal cells subjected to 24 hours of serum withdrawal, HV-3 treatment reduced the release of high mobility group box 1 (HMGB1) and lactate dehydrogenase (LDH), two indicators of cell death (FIGS. 3C and D). However, HV-3 had no effects on apoptosis, as evaluated by the activity of caspase-3, under the same cultured conditions. VCP is an essential regulator of the ERAD and ER-related unfolded protein response. We found that HV-3 treatment had no effects on the ER stress response, excluding the possibility that the protection provided by HV-3 on mitochondria is the result of a secondary consequence of the inhibition of ER stress.

Neurons derived from HD patient induced pluoripotent stem cells (HD-iPS cells) exhibited mitochondrial damage and increased cell death. In neurons immuno-positive for both anti-DARPP-32 (a marker of medium spiny neurons) and anti-Tubulin β-III (a marker of mature neurons), treatment with HV-3 (1 µM/day for 5 days starting 30 days after initiation of neuronal differentiation) significantly reduced neurite shortening compared to patient neurons treated with control peptide TAT (FIG. 4E, F). Further, HV-3 treatment suppressed neuronal cell death in these patient-derived neurons subjected to growth factor withdrawal (FIG. 4H). The neuroprotective effects of HV-3 were consistently associated with improved mitochondrial membrane potential and mitochondrial length along neurite (FIG. 3G). Taken together, the above results demonstrate that treatment with HV-3 protects against mitochondrial damage and neuronal cell death under HD-associated conditions.

Interestingly, we found that the peptide HV-3 had only minor effects on VCP mitochondrial levels, mitochondrial membrane potential, and morphology, as well as cell survival rate in wild-type counterparts of the above HD experimental models (FIGS. 2, 3), which is likely the result of less binding between VCP and wt Htt under basal conditions (FIG. 1G). Normal and mutant polyglutamine proteins interact with VCP and only mutant proteins specifically affect dynamism of VCP and impair its function, thus it is also possible that disruption of wtHtt/VCP interaction results in minor physiological impact.

Collectively, our findings not only show that mtHtt is required for VCP recruitment to mitochondria, but also suggest that HV-3 is useful for testing the biological significance of mitochondria-accumulated VCP in HD.

VCP Translocation to Mitochondria by mtHtt Impaired Mitochondria-Related Autophagy in HD Models In Vitro and In Vivo How does mtHtt-induced VCP mitochondrial accumulation mediate mitochondrial dysfunction and cell death? Apoptosis and autophagic cell death are manifested in HD neuropathology. Blocking VCP recruitment to mitochondria by treatment with HV-3 did not affect apoptotic cell death. In contrast, down-regulation of VCP by VCP siRNA in mouse HdhQ111 striatal cells reduced the levels of mitochondria-associated LC3 II, a marker of mitophagy, (FIG. 4A). Moreover, expression of Flag-VCP in wild-type mouse striatal cells induced GFP-LC3B association with mitochondria, which could be inhibited by treatment with HV-3 (FIG. 4B). Thus, we speculated that mtHtt-induced VCP accumulation on mitochondria triggers mitochondria-associated autophagy.

We treated HdhQ7 and HdhQ111 striatal cells with peptide HV-3 and control peptide TAT, and determined autophagic activity in these cells. In HdhQ111 cells, we observed an increased number of GFP-LC3B puncta, a specific marker for autophagosomes, and hyperactivity of lysosome enzyme Cathepsin B, both of which were reduced by treatment with HV-3 (FIG. 4C, D). Similarly, neurons derived from HD patient-iPS cells exhibited lower mitochondrial mass and lysosome hyperactivity, whereas treatment with HV-3 corrected these aberrant events (FIG. 4E, F). Further, we examined the ultrastructure of striatal mitochondria in YAC128 mice. Relative to that in wild-type littermates, we observed an increase in the number of mitophagosomes in 9-month-old YAC128 mice treated with the control peptide TAT, which was reduced by HV-3 treatment (FIG. 4G). The above findings suggest that inhibition of VCP mitochondrial accumulation in HD by treatment with peptide HV-3 suppress excessive mitophagy and improve mitochondrial quality.

LC3 in mammals or Atg8 in yeast play a key role in both autophagosome membrane biogenesis and cargo recognition. In yeast, Atg32 functions as a receptor on mitochondria to initiate mitophagy through interaction with Atg8. Similarly, mammalian mitophagic adaptors, such as FUNDC1, p62, BNIP3, and AMBRA1, all bind to LC3 via a typical linear motif with a core consensus sequence of W/Y/F xx L/I/V, also called LC3-interacting region (LIR). Given the above findings, we hypothesized that VCP might bind to LC3 on mitochondria to enhance mitophagosome production. Using an iLIR server, we found that VCP contains two segments of sequence (LEAYRPIR (SEQ ID NO: 11) and AVEFKVVE (SEQ ID NO: 12) located in the β stands of the N terminal (FIG. 5A) that fulfill the characteristics of the LIR. To determine if VCP binds to LC3 via putative LIR motifs, we generated two mutants (VCP-YI$^{AA}$ and VCP-FV$^{AA}$) in which Y/I and F/V were all replaced by alanine. Because of higher transfection efficiency, we first used HeLa cells to determine the effects of these mutants. In HeLa cells co-expressing Myc-VCP and GFP-LC3B, we performed IP analysis of mitochondrial fractions with anti-GFP antibody followed by IB with anti-Myc antibody. We found that Myc-VCP was bound to GFP-LC3B in the mitochondrial fractions of cells (FIG. 5B). Expression of either VCP-YI$^{AA}$ or VCP-FV$^{AA}$ abolished the VCP/LC3 interaction relative to cells expressing VCP$^{WT}$ (FIG. 5B). Moreover, expression of VCP-YI$^{AA}$ or VCP-FV$^{AA}$ reduced LC3 association with the mitochondria (FIG. 5C) and increased mitochondrial mass (FIG. 5D) compared to cells expressing VCP$^{WT}$. These data demonstrate that mitochondria-accumulated VCP accelerates mitophagy by interacting with LC3 through the LIRs.

To determine direct consequence of VCP mitochondrial accumulation on mitophagy and cell survival, we generated a construct encoding VCP fused to a flag-vector containing a mitochondrial targeting sequence (MTS) (flag-VCP$^{mt}$). In HeLa cells expressing flag-VCP$^{mt}$, we confirmed the enrichment of flag-VCP$^{mt}$ on mitochondria. We further observed that expression of flag-VCP$^{mt}$ induced a relocalization of the mitochondria network, forming mitochondrial aggregates which is an intermediate step of mitophagy, around the perinuclear envelope. The occurrence of mitochondrial aggregates in cells expressing flag-VCp$^{mt}$ increased by approximately sevenfold relative to cells not expressing flag-VCP$^{mt}$. Moreover, the presence of flag-VCP$^{mt}$ in cells decreased mitochondrial membrane potential and mitochondrial mass, but induced an increase in the percentage of GFP-LC3B colocalizing with Tom20-labeled mitochondria. Upon treatment with bafilomycin A (BFA) to prevent autophagosome-lysosome fusion, flag-VCP$^{mt}$ expression elevated the autophagic flux of the mitochondria, indicating increased rate of mitochondrial degradation. We then expressed the flag-VCP$^{mt}$ and wild-type vector in rat primary striatal neurons. Expression of flag-VCP$^{mt}$ elicited mitochondrial aggregates and caused neurite shortening of medium spiny neurons that were labeled by anti-DARPP-32 antibody (FIG. 5E, F). Thus, mitochondria-accumulated VCP caused mitochondrial and neuronal damage, at least in part, via impairment of the mitophagic process.

Treatment with HV-3 Reduced Behavioral Phenotypes of HD in HD R6/2 and YAC128 Mice We next examined if blocking VCP accumulation on the mitochondria provides neuroprotection in in vivo animal models of HD. We treated HD R6/2 mice and YAC128 mice with control peptide TAT or peptide HV-3 using the protocols shown in Supplemental FIG. 5.

We first examined the effects of HV-3 treatment on behavioral phenotypes of HD in both R6/2 and YAC128 mice. HD R6/2 mice treated with the control peptide TAT exhibited decreased horizontal and vertical activities as well as less total traveled distance in the test of spontaneous locomotion when evaluated at the age of 13 weeks, whereas treatment with HV-3 dramatically corrected these motor deficits (FIG. 6A). The severity of clasping behavior in R6/2 mice treated with HV-3 was significantly lower than those treated with the control peptide TAT over the four-week observation period (FIG. 6A). HV-3 treatment also resulted in increased body weight and survival rate of R6/2 mice (FIG. 6B, C). The treatment had no effects on motor ability, body weight, or life span in wild-type mice (FIG. 6A-C), suggesting a lack of toxicity of the peptide treatment.

The YAC128 mice exhibit progressive motor abnormalities as well as late-stage selective striatal neuron loss, closely recapitulating a chronic feature of neuropathology seen in human HD. We examined the long-term treatment effects of HV-3 on the behavioral outcomes in YAC128 mice. Consistent with previous studies, YAC128 mice progressively exhibited deficits in motor activities; they showed gradually decreasing motor coordination activity on the rotarod and defects in general motility examined by locomotor activity chambers. Significantly, sustained treatment with HV-3 improved general movement activity and rotarod performance of YAC128 mice starting at the age of 6 months, and the protection was lasted until the age of 12 months (FIG. 6D, E). Again, the treatment did not affect motor activity in wild-type mice from 3 to 12 months of age.

Sustained Treatment with HV-3 Reduced Neuropathology in HD R6/2 and YAC128 Mice In HD patients, medium spiny neurons in the striatum are particularly susceptible to degeneration. The levels of dopamine signaling protein, DARPP-32, enriched in these cells are decreased in the striatum of HD patients and mouse models. Thus, DARPP-32 has been used as a marker to assess the neuronal degeneration in HD mouse models. Western blot analysis of striatal extracts revealed a significant reduction of DARPP-32 protein levels in both R6/2 and YAC128 mice. HV-3 treatment significantly increased DARPP-32 levels in the two mouse models (FIG. 7A). In HD R6/2 mice, we consistently observed a decrease in the area occupied by DARPP-32-immunostained cells in the striatum, which was increased by HV-3 treatment (FIG. 7B, C). To further assess whether HV-3 treatment can suppress neurodegenerative pathology in HD, we conducted unbiased stereology analyses to measure the number of striatal neurons in YAC128 mice at the age of 12 months. We found that treatment with HV-3 significantly increased the number of neurons positive for anti-NeuN immunostaining in the dorsolateral striatum (FIG. 7D).

The findings from both the fragment and full-length mtHtt transgenic mouse models demonstrate that blocking mtHtt-induced VCP mitochondrial accumulation by peptide HV-3 greatly reduced neuropathology and motor deficits that are associated with HD.

HV-3 Dose Response in Animal Models of R6/2 Mice

R6/2 mice express a fragment of mutant Huntingtin and the mouse line exhibits severe neuropathology of Huntington's disease. The R6/2 mice have short life span and most of animals die before 15 weeks of age. We determined the survival rate of R6/2 mice by the age of 13 weeks. We treated the R6/2 mice with HV-3 at 0.5, 1 and 3 mg/kg/day using osmotic mini pump (subcutaneously administration), and found that HV-3 at 3 mg/kg/day dramatically improved the survival of R6/2 mice (FIG. 9). Therefore, we used 3 mg/kg/day of HV-3 in our rest of studies. To wildtype mice, we treated mice with either TAT or HV-3 at 3 mg/kg/day. There was no difference on survival rate in the groups treated with TAT or HV-3.

Example 2

Treatment with HV-3 Corrected Aberrant Mitochondrial Intermediates in HD Mouse Plasma Deficits in energy metabolism, attributable to mitochondrial dysfunction, is an early event in HD patients. To determine the effects of HV-3 treatment on mitochondrial metabolic activity in vivo, we used target metabolomics analysis of HD mouse plasma to profile the intermediates of the mitochondrial tricarboxylic acid (TCA) cycle, a central metabolic pathway within mitochondria for eukaryotes. LC-MS/MS analysis revealed that 8 out of 16 intermediates derived from the TCA cycle were decreased in R6/2 mouse plasma relative to those in wild-type mice (Table 1), suggesting a decrease in mitochondrial metabolic activity. Treatment with HV-3 in R6/2 mice significantly increased the plasma content of $NAD^+$, FAD, and citrate (Table 1). In contrast, HV-3 treatment had no effects on the intermediates derived from amino acid metabolism, although some of intermediates in this pathway were altered in HD mice relative to those in wild-type mice (Table 2). $NAD^+$ and FAD are central biomolecules involved in energy production and mitochondrial metabolic activity; declines in NAD and FAD levels reflect decreased mitochondrial number, density, and activity. Thus, the findings here in parallel demonstrated that mtHtt-induced mitochondria-accumulated VCP causes mitochondrial dysfunction and global energy deficits in HD, leading to neuronal cell death. Because the depletion in $NAD^+$ was noted in HD patient cells and blood, normalization of $NAD^+$ content in HD mouse plasma by HV-3 treatment might provide a biomarker amenable for therapeutic intervention.

TABLE 1

Content of Mitochondiral intermediates in HD R6/2 mouse plasma
Concentration (μg/ml mouse plasma)

| Group | Asparate | -Acetyl-Aspartal | Cis-Aconitate | Citrate | Ketoglutarate | Malate | Succinate | Fumarate | Pyruvate | Isocitrate | NAD+ | FAD |
|---|---|---|---|---|---|---|---|---|---|---|---|---|
| Wt/Veh | 1.31 ± 0.31 | 0.93 ± 0.08 | 0.49 ± 0.05 | 31.31 ± 2.18 | 11.25 ± 1.70 | 3.36 ± 0.41 | 15.63 ± 1.79 | 3.14 ± 0.34 | 7.05 ± 0.78 | 5.66 ± 0.56 | 0.07 ± 0.01 | 0.25 ± 0.02 |
| Wt/HV-3 | 0.98 ± 0.20 | 0.98 ± 0.14 | 0.45 ± 0.05 | 33.66 ± 2.74 | 11.66 ± 2.15 | 4.45 ± 0.64 | 18.87 ± 2.12 | 3.84 ± 0.51 | 10.30 ± 1.15 | 7.24 ± 0.78 | 0.07 ± 0.01 | 0.29 ± 0.02 |
| HD/Veh | 1.31 ± 0.19 | 0.75 ± 0.08 | 0.47 ± 0.06 | 24.52 ± 1.48 | 6.23 ± 1.11 | 3.31 ± 0.43 | 10.32 ± 1.34* | 2.57 ± 0.34 | 12.71 ± 1.32* | 8.12 ± 0.80* | 0.04 ± 0.004* | 0.20 ± 0.02* |
| HD/HV3 | 1.90 ± 0.23 | 0.84 ± 0.07 | 0.48 ± 0.05 | 31.03 ± 2.02# | 5.88 ± 0.63 | 4.07 ± 0.46 | 9.07 ± 1.36 | 3.32 ± 0.41 | 13.74 ± 3.19 | 9.63 ± 1.05 | 0.07 ± 0.01# | 0.28 ± 0.03# |

*p < 0.05 vs. wildtype mice treated with TAT;
p < 0.0 vs. HP mice treated with TAT Table 1 listed the changes of intermediates of mitochondrial TCA cycle in HD R6/2 mouse plasma. Sixteen intermediates derived from mitochondrial TCA cycle were determined by LC/MS/MS using the standard substrates. We found that 8 intermediates derived from the TCA cycle were decreased in HD R6/2 mouse plasma relative to those from wild-type littermates. HV-3 treatment specifically corrected the amount of $NAD^+$, FAD, and citrate. In addition, four intermediates (ccetyl-CoA, succinyl-CoA, oxaloacetate, and ketobutyrate) were not detectable in the mouse plasma. Data are mean±SE, n=15 mice/group. Data are analyzed by one-way ANOVA with post hoc Turkey test.

Method

Target Metabolomics Analysis

Mouse plasma was harvested at the age of 12 weeks from HD R6/2 mice and wild-type littermates. Mouse plasma was mixed with internal standards followed by an addition of methanol to precipitate the sample protein by centrifuging at 12,000 rpm. After centrifugation, supernatant was dried under nitrogen flow and the dried pellet was suspended using 80 µl HPLC grade water. Twenty µl of suspended sample was injected into the HPLC system which is directly

TABLE 2

Concentration of Intermediates of amino acid metabolism in HD R6/2 mouse plasma

| | Concentration in mouse plasma (µM) | | | | | | | | |
|---|---|---|---|---|---|---|---|---|---|
| | Alanine | Serine | Threonine | Proline | Valine | Leucine | Iso-Leucine | Aspartic Acid | Glutamine |
| WT | 153.6 +/− 8.5 | 61.5 +/− 5.3 | 36.6 +/− 3.1 | 88.2 +/− 8.2 | 50.6 +/− 5.6 | 11.3 +/− 1.4 | 64.2 +/− 5.9 | 3.0 +/− 0.6 | 394.1 +/− 30.6 |
| Wt/HV-3 | 130.0 +/− 14.7 | 56.1 +/− 5.8 | 31.3 +/− 2.6 | 90.3 +/− 16.3 | 39.5 +/− 2.8 | 13.8 +/− 1.6 | 72.2 +/− 5.9 | 3.2 +/− 0.4 | 370.0 +/− 15.3 |
| HD | 149.6 +/− 19.4 | 120.9 +/− 23.6* | 54.3 +/− 9.3* | 167.4 +/− 22.6* | 62.2 +/− 7.9 | 17.5 +/− 2.3* | 93.9 +/− 10.9* | 4.6 +/− 0.5 | 637.7 +/− 77.1* |
| HD/HV3 | 169.0 +/− 16.0 | 127.4 +/− 9.5 | 67.3 +/− 7.8 | 171.8 +/− 7.2 | 80.0 +/− 8.1 | 15.5 +/− 1.7 | 84.3 +/− 6.1 | 4.1 +/− 0.3 | 627.7 +/− 45.1 |
| | Concentration in mouse plasma (µM) | | | | | | | | |
| | Alanine | Serine | Threonine | Proline | Valine | Leucine | Iso-Leucine | Aspartic Acid | Glutamine |
| WT | 250.8 +/− 18.0 | 11.7 +/− 2.1 | 13.7 +/− 0.9 | 77.5 +/− 5.8 | 31.9 +/− 1.9 | 158.6 +/− 19.1 | 35.6 +/− 2.8 | 19.9 +/− 2.5 | 28.4 +/− 4.2 |
| Wt/HV-3 | 242.9 +/− 17.2 | 7.8 +/− 1.9 | 14.2 +/− 1.1 | 78.1 +/− 5.7 | 33.6 +/− 1.9 | 162.8 +/− 19.3 | 35.6 +/− 2.6 | 19.8 +/− 2.0 | 29.2 +/− 2.9 |
| HD | 354.2 +/− 26.9* | 8.1 +/− 4.8 | 17.0 +/− 1.1* | 103.7 +/− 5.3* | 39.9 +/− 1.9* | 365.2 +/− 48.1* | 43.4 +/− 2.5 | 25.3 +/− 2.9 | 28.2 +/− 3.5* |
| HD/HV3 | 376.6 +/− 17.5 | 10.6 +/− 2.7 | 19.9 +/− 1.3 | 102.8 +/− 3.2 | 43.8 +/− 1.4 | 345.5 +/− 18.4 | 42.5 +/− 2.1 | 31.4 +/− 2.9 | 25.2 +/− 2.2 |

*$p < 0.05$ vs. wildtype mice treated with TAT

Table 2 listed the intermediates of amino acid metabolic pathway. Eighteen intermediates derived from amino acid metabolism were determined by LC/MS/MS method. HV-3 treatment had no statistic effects on these intermediates. These data further demonstrated a selective role of HV-3 on mitochondrial energy metabolic activity. Data are mean±SE, n=10 mice/group. Data are analyzed by one-way ANOVA with post hoc Turkey test.

HD R6/2 mice and wild-type littermates were treated with control peptide TAT or HV-3 peptides at 3 mg/kg/day from the age of 5 weeks to 13 weeks. Plasma was harvested at the age of 12 weeks. Target metabolomics analysis of mouse plasma was conducted as described in Method. In this study, we focused on mitochondrial TCA cycle and amino acid metabolic pathways for the analysis, because failures in these two pathways in HD patients were previously reported.

interfaced with a triple-quadrupole mass spectrometer. The HPLC eluent was automatically injected into the mass spectrometer and the compounds in the eluent were analyzed with electrospray ionization (at positive or negative charged) tandem mass spectrometry using the scan termed multiple reaction monitoring. The analysis was conducted at the Cleveland Clinic Lerner Research Center Metabolomics core facility by individuals blind to the treatment groups.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

I claim:

1. A method of inhibiting valosin-containing protein (VCP) accumulation in mitochondria of a nerve cell, the method comprising:
   administering to the nerve cell a therapeutic peptide having the amino acid sequence of SEQ ID NO: 3.

2. The method of claim 1, wherein the therapeutic peptide is linked to a transport moiety.

3. The method of claim 2, wherein the transport moiety is an HIV Tat transport moiety.

4. A method of treating Huntington's disease in a subject in need thereof, the method comprising:
   administering to the subject a therapeutic peptide having the amino acid sequence of SEQ ID NO: 3.

5. The method of claim 4, wherein the therapeutic peptide includes a transport moiety that is linked to the therapeutic peptide.

6. The method of claim 5, wherein the transport moiety is an HIV Tat transport moiety.

7. The method of claim 4, wherein the therapeutic agent is administered systemically to a subject being treated.

8. The method of claim 4, wherein the therapeutic agent is administered at an amount effective to increase plasma levels of NAD+, FAD, and/or citrate in the subject.

9. The method of claim 8, wherein the therapeutic agent is administered at about 3 mg/kg/day to the subject.

* * * * *

SEQUENCE LISTING

<160> NUMBER OF SEQ ID NOS: 15

<210> SEQ ID NO 1
<211> LENGTH: 7
<212> TYPE: PRT
<213> ORGANISM: Homo sapiens

<400> SEQUENCE: 1

Asp Leu Phe Val Leu Arg Gly
1               5

<210> SEQ ID NO 2
<211> LENGTH: 7
<212> TYPE: PRT
<213> ORGANISM: Homo sapiens

<400> SEQUENCE: 2

Asp Ile Phe Leu Val Arg Gly
1               5

<210> SEQ ID NO 3
<211> LENGTH: 8
<212> TYPE: PRT
<213> ORGANISM: Homo sapiens

<400> SEQUENCE: 3

His Val Leu Val Met Cys Ala Thr
1               5

<210> SEQ ID NO 4
<211> LENGTH: 8
<212> TYPE: PRT
<213> ORGANISM: Homo sapiens

<400> SEQUENCE: 4

His Val Ile Val Met Ala Ala Thr
1               5

<210> SEQ ID NO 5
<211> LENGTH: 10
<212> TYPE: PRT
<213> ORGANISM: Homo sapiens

<400> SEQUENCE: 5

Gly Arg Lys Lys Arg Arg Gln Arg Arg Arg
1               5                   10

<210> SEQ ID NO 6
<211> LENGTH: 18
<212> TYPE: PRT
<213> ORGANISM: Homo sapiens

<400> SEQUENCE: 6

Gly Arg Lys Lys Arg Arg Gln Arg Arg Arg His Val Leu Val Met Cys
1               5                   10                  15

Ala Thr

<210> SEQ ID NO 7
<211> LENGTH: 13
<212> TYPE: PRT
<213> ORGANISM: Homo sapiens

<400> SEQUENCE: 7

Gln Gln His Val Leu Val Met Cys Ala Thr Ala Phe Tyr

```
1               5                    10

<210> SEQ ID NO 8
<211> LENGTH: 13
<212> TYPE: PRT
<213> ORGANISM: Mus musculus

<400> SEQUENCE: 8

Gln Gln His Val Leu Val Met Cys Ala Thr Ala Phe Tyr
1               5                    10

<210> SEQ ID NO 9
<211> LENGTH: 13
<212> TYPE: PRT
<213> ORGANISM: Rattus rattus

<400> SEQUENCE: 9

Gln Gln His Val Leu Val Met Cys Ala Thr Ala Phe Tyr
1               5                    10

<210> SEQ ID NO 10
<211> LENGTH: 13
<212> TYPE: PRT
<213> ORGANISM: Danio rerio

<400> SEQUENCE: 10

Gln Gln His Val Leu Val Met Cys Ala Val Ala Phe Tyr
1               5                    10

<210> SEQ ID NO 11
<211> LENGTH: 8
<212> TYPE: PRT
<213> ORGANISM: Homo sapiens

<400> SEQUENCE: 11

Leu Glu Ala Tyr Arg Pro Ile Arg
1               5

<210> SEQ ID NO 12
<211> LENGTH: 8
<212> TYPE: PRT
<213> ORGANISM: Homo sapiens

<400> SEQUENCE: 12

Ala Val Glu Phe Lys Val Val Glu
1               5

<210> SEQ ID NO 13
<211> LENGTH: 8
<212> TYPE: PRT
<213> ORGANISM: Homo sapiens

<400> SEQUENCE: 13

Ser Gly Ser Trp Gln Ala Ile Gln
1               5

<210> SEQ ID NO 14
<211> LENGTH: 8
<212> TYPE: PRT
<213> ORGANISM: Homo sapiens

<400> SEQUENCE: 14

Asp Asp Ser Tyr Glu Val Leu Asp
1               5
```

```
<210> SEQ ID NO 15
<211> LENGTH: 8
<212> TYPE: PRT
<213> ORGANISM: Homo sapiens

<400> SEQUENCE: 15

Asp Asp Asp Trp Thr His Leu Ser
1               5
```